US006576747B1

(12) United States Patent
Carlini et al.

(10) Patent No.: US 6,576,747 B1
(45) Date of Patent: Jun. 10, 2003

(54) PROCESSES FOR PREPARING DIANTHRANILATE COMPOUNDS AND DIAZOPYRIDONE COLORANTS

(75) Inventors: Rina Carlini, Mississauga (CA); James M. Duff, Mississauga (CA); Stephen G. Robinson, Burlington (CA); George Liebermann, Mississauga (CA); Roger E. Gaynor, Oakville (CA); Tania Pereira, Mississauga (CA); Jeffrey H. Banning, Hillsboro, OR (US); James D. Mayo, Mississauga (CA)

(73) Assignee: Xerox Corporation, Stamford, CT (US)

( * ) Notice: Subject to any disclaimer, the term of this patent is extended or adjusted under 35 U.S.C. 154(b) by 0 days.

(21) Appl. No.: 10/185,261

(22) Filed: Jun. 27, 2002

(51) Int. Cl.[7] .................... C09B 35/031; C07C 209/62
(52) U.S. Cl. ................ 534/649; 534/757; 534/DIG. 2; 560/49
(58) Field of Search ................ 534/649, 757, 534/DIG. 2; 560/49

(56) References Cited

U.S. PATENT DOCUMENTS

| | | | |
|---|---|---|---|
| 3,929,863 A | * 12/1975 | Blahak et al. | 560/50 |
| 3,957,749 A | 5/1976 | von Brachel et al. | 260/156 |
| 4,216,145 A | 8/1980 | Battisti et al. | 260/156 |
| 4,247,456 A | 1/1981 | von Brachel et al. | 260/156 |
| 4,359,418 A | 11/1982 | Lienhard et al. | 260/156 |
| 4,644,058 A | 2/1987 | Shimidzu et al. | 534/635 |
| 4,734,349 A | 3/1988 | Chapman et al. | 430/106 |
| 4,889,560 A | 12/1989 | Jaeger et al. | 106/27 |
| 4,889,761 A | 12/1989 | Titterington et al. | 428/195 |
| 4,994,564 A | 2/1991 | Etzbach et al. | 534/766 |
| 5,006,170 A | 4/1991 | Schwarz et al. | 106/20 |
| 5,037,964 A | * 8/1991 | Moser et al. | 534/608 |
| 5,041,413 A | 8/1991 | Evans et al. | 503/227 |
| 5,372,852 A | 12/1994 | Titterington et al. | 427/288 |
| 5,621,022 A | 4/1997 | Jaeger et al. | 523/161 |
| 5,827,918 A | 10/1998 | Titterington et al. | 524/590 |
| 5,902,841 A | 5/1999 | Jaeger et al. | 523/161 |
| 5,919,839 A | 7/1999 | Titterington et al. | 523/161 |
| 5,929,218 A | 7/1999 | Lee et al. | 534/772 |

FOREIGN PATENT DOCUMENTS

| | | |
|---|---|---|
| DE | 2 040 644 | 12/1975 |
| DE | 3538517 A1 | 5/1986 |
| EP | 0 013 956 | 8/1980 |
| EP | 0 023 770 A1 | 2/1981 |
| EP | 0 083 553 A1 | 12/1982 |
| EP | 0 142 863 B1 | 5/1985 |
| EP | 0 172 283 A1 | 2/1986 |
| EP | 0 247 737 A1 | 12/1987 |
| EP | 0 302 401 A1 | 7/1988 |
| EP | 0 314 002 B1 | 9/1991 |
| EP | 0 468 647 B1 | 1/1992 |
| EP | 0 404 493 B1 | 5/1994 |
| EP | 0 319 234 B1 | 3/1995 |
| EP | 0 524 637 B1 | 3/1996 |
| EP | 0 529 282 B1 | 10/1996 |
| EP | 0 706 679 B1 | 9/1997 |
| EP | 0 844 287 B1 | 5/2000 |
| EP | 1 125 990 A1 | 8/2001 |
| EP | 1 168 046 A1 | 1/2002 |
| GB | 2 008 606 A | 6/1979 |
| GB | 1 559 001 | 1/1980 |
| IN | 147868 | 7/1980 |
| KR | 119563 | 8/1997 |
| WO | WO 95/00885 | 1/1995 |
| WO | WO 99/43754 | 9/1999 |
| WO | WO 01/21714 A2 | 3/2001 |
| WO | WO 01/09256 A1 | 8/2001 |

OTHER PUBLICATIONS

Copending application U.S. Ser. No. 10/185,994 (Attorney Docket No. D/A2234), filed Jun. 27, 2002, entitled "Dimeric Azo Pyridone Colorants," by Rina Carlini et al.

Copending application U.S. Ser. No. 10/184,269 (Attorney Docket No. D/A2236), filed Jun. 27, 2002, entitled "Phase Change Inks Containing Dimeric Azo Pyridone Colorants" by Bo Wu et al.

(List continued on next page.)

*Primary Examiner*—Fiona T. Powers
(74) *Attorney, Agent, or Firm*—Judith L. Byorick

(57) ABSTRACT

Disclosed is a process for preparing dianthranilate compounds which comprises (a) admixing reactants as follows: (1) a diol of the formula $R_1(OH)_2$, wherein $R_1$ is an alkylene group having at least about 20 carbon atoms, and wherein the —OH groups are primary or secondary, (2) isatoic anhydride, present in an amount of at least, about 2 moles of isatoic anhydride per every one mole of diol, (3) a catalyst which is 1,4-diazabicyclo [2.2.2]octane, N,N,N',N'-tetramethylethylene diamine, or a mixture thereof, said catalyst being present in an amount of at least about 0.2 mole of catalyst per every one mole of diol, and (4) a solvent; and (b) heating the mixture thus formed to form a dianthranilate compound of the formula

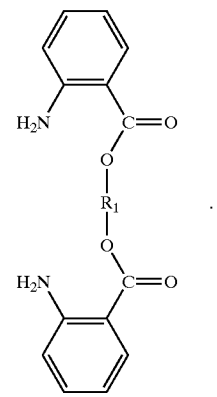

Also disclosed is a process for preparing diazopyridone colorants which comprises (I) preparing a dianthranilate compound by the aforementioned method, (II) reacting the dianthranilate compound with nitrosylsulfuric acid to form a diazonium salt, and (III) reacting the, diazonium salt with a pyridone compound to form a diazopyridone compound.

26 Claims, No Drawings

OTHER PUBLICATIONS

Copending application U.S. Ser. No. 10/185,264 (Attorney Docket No. D/A2237), filed Jun. 27, 2002, entitled "Phase Change Inks Containing Azo Dimeric Pyridone Colorants" by Jeffery H. Banning et al.

Copending application U.S. Ser. No. 10/186,024 (Attorney Docket No. D/A2238), filed Jun. 27, 2002, entitled "Azo Pyridone Colorants," by Jeffery H. Banning etal.

Copending application U.S. Ser. No. 10/185,597 (Attorney Docket No. D/A2239), filed Jun. 27, 2002, entitled "Process for Preparing Substituted Pyridone Compounds," by James D. Mayo et al.

Copending application U.S. Ser. No. 10/186,023 (Attorney Docket No. D/A2281), filed Jun. 27, 2002, entitled "Dimeric Azo Pyridone Colorants," by Rina Carlini et al.

Copending application U.S. Ser. No. 10/184,266 (Attorney Docket No. D/A2281Q), filed Jun. 27, 2002, entitled "Phase Change Inks Containing Dimeric Azo Pyridone Colorants," by Bo Wu et al.

Copending application U.S. Ser. No. 10/185,828 (Attorney Docket No. D/A2278), filed Jun. 27, 2002, entitled "Method for Making Dimeric Azo Pyridone Colorants," by Rina Carlini et al.

English Abstract for German Patent Publication DE 2 902 740.

"Polyamines Containing Ester Groups as Structural Components in Polyurethane Chemistry", J. Blahak et al., Angew. Makromol. Chem. (1972), vol. 26, pp. 29 to 45.

"The Chemistry of Isatoic Anhydride," G. M. Coppola, *Synthesis*, p. 505 (1980).

"Isatoic Anhydride. IV. Reactions with Various Nucleophiles," R. P. Staiger et al., *J. Org. Chem.*, vol. 24, p. 1214 (1959).

English Abstract for German Patent Publication DE 19646430.

English Abstract for German Patent Publication DE 19646429.

English Abstract for German Patent Publication DE 19647869.

English Abstract for Japanese Patent Publication JP 3192158.

"Preparation and Evaluation of Yellow Pigments Based on H–Pyridone and Esters of Aminoterephthalic Acid," P. Slosar et al., CHEMagazin, vol. 9, No. 6, pp. 8–11 (1999) (Not translated).

"Synthesis, Morphology, and Optical Properties of Tetrahedral Oligo(phenylenevinylene) Materials," S. Wang et al., *J. Am. Chem. Soc.*, vol. 120, p. 5695 (2000).

"Syntheses of Amphiphilic Diblock Copolymers Containing a Conjugated Block and Their Self–Assembling Properties," H. Wang et al., *J. Am. Chem. Soc.*, vol. 122, p. 6855 (2000).

"Crystal Engineering of Conjugated Oligomers and the Spectral Signature of π Stacking in Conjugated Oligomers and Polymers," A. Koren et al., *Chem. Mater.*, vol. 12, p. 1519 (2000).

"Investigation of the Reaction Conditions for the Synthesis of 4,6–Disubstituted–3–cyano–2–pyridones and 4–Methyl–3–cyano–6–hydroxy–2–pyridone," D. Z. Mijin et al., *J. Serb. Chem. Soc.*, vol. 59, No. 12, p. 959 (1994).

Synthesis of Isoquinoline Alkaloids. II. The Synthesis and Reactions of 4–Methyl–3–pyridinecarboxaldehyde and Other 4–Methyl–3–substituted Pyridines, J. M. Bobbitt et al., *J. Org. Chem.*, vol. 25, p. 560 (1960).

"Synthesis and Dyeing Characteristics of 5–(4–Arylazophenyl) azo–3–cyano–4–methyl–6–hydroxy–2–pyridones," J. Kanhere et al., *Indian Journal of Textile Research*, vol. 13, p. 213 (1988).

English Abstract and description (not translated) for German Patent Publication DE 3543360.

English Abstract for Japanese Patent Publication JP 2001214083.

English Abstract for German Patent Publication DE 3505899.

"Yellow to Violet Azo–N–Substituted Pyridinone Disperse Dyes for Synthetic Fibers," I.M.S. Mamak, *Indian*, pp. 1–11 (1980) (Indian Patent Publication 147527).

English Abstract for Japanese Patent Publication JP2000062327.

English Abstract for Japanese Patent Publication JP60152563.

"Synthesis of 3–Cyano–6–hydroxy–5–(2–[perfluoroalkyl)phenylazo]–2–pyridones and their Application for Dye Diffusion Thermal Transfer Printing," *Bull. Chem. Soc. Jpn.*, vol. 66, Iss. 6, Pp. 1790–4, (1993).

English Abstract for Chinese Patent Publication CN1115773.

English Abstract for German Patent Publication DE 3447117.

English Abstract for Japanese Patent Publication JP 5331382.

English Abstract for Japanese Patent Publication JP 63210169.

English Abstract for Japanese Patent Publication JP 63199764.

English Abstract for Japanese Patent Publication JP 63199763.

English Abstract for Japanese Patent Publication JP 63199762.

English Abstract for Japanese Patent Publication JP 63199761.

English Abstract for Japanese Patent Publication JP 63199760.

English Abstract for Japanese Patent Publication JP 63071392.

English Abstract for Japanese Patent Publication JP 61181865.

English Abstract for Japanese Patent Publication JP 61036366.

English Abstract for Japanese Patent Publication JP 60112862.

English Abstract for Japanese Patent Publication JP 60112861.

English Abstract for Japanese Patent Publication JP 58149953.

English Abstract for Japanese Patent Publication JP 56092961.

English Abstract for Japanese Patent Publication JP 56026957.

English Abstract for Japanese Patent Publication JP 55099958.

English Abstract for Japanese Patent Publication JP 96 11443 (JP8011443).

English Abstract for Japanese Patent Publication JP 93169849 (JP169849).

English Abstract for Japanese Patent Publication JP 93 51536 (JP5051536).

English Abstract for Japanese Patent Publication JP 90185569 (JP2185569).
English Abstract for Japanese Patent Publication JP 87290762 (JP62290762).
English Abstract for Japanese Patent Publication JP 86244595 (JP61244595).
English Abstract for Spanish Patent Publication 475254 (Equivalent of Italian Patent Publication IT 1088895).
English Abstract for German Patent Publication DE 2727809.
"Colour and Constitution of Azo Dyes Derived from 2–Thioalkyl–4,6–Diaminopyrimidines and 3–Cyano–1,4–dimethyl–6–hydroxy–2–pyridone as Coupling Components," L. Cheng et al., *Dyes and Pigments*, vol. 7, No. 5, pp. 373–388 (1986).
English Abstract for Japanese Patent Publication JP 63039380.
English Abstract for Japanese Patent Publication JP 54102328.
English Abstract for Japanese Patent Publication JP 54070337.
"Trends in Modern Dye Chemistry. Part 10," N. R. Ayyangar and K. V. Srinivasan, *Colourage*, vol. 37, No. 2, pp. 29–30 (Jan. 16, 1990).
English Abstract for Japanese Patent Publication JP 05169854.
English Abstract for Japanese Patent Publication JP 04292988.
English Abstract for Japanese Patent Publication JP 63161060.
English Abstract for Japanese Patent Publication JP 61244595.
English Abstract for Japanese Patent Publication JP 00239549 (JP2000239549).
English Abstract for Japanese Patent Publication JP 11269402.
English Abstract for Japanese Patent Publication JP 09041267.
English Abstract for Japanese Patent Publication JP 08039941.
English Abstract for Japanese Patent Publication JP 06294909.
English Abstract for Japanese Patent Publication JP 06122829.
English Abstract for Japanese Patent Publication JP 05255602.
English Abstract for Japanese Patent Publication JP 05051536.
English Abstract for Japanese Patent Publication JP 04235093.
English Abstract for European Patent Publication EP 0 063 275.
English Abstract for German Patent Publication DE 2606506.

* cited by examiner

PROCESSES FOR PREPARING DIANTHRANILATE COMPOUNDS AND DIAZOPYRIDONE COLORANTS

Cross-reference is made to the following applications:

Copending application U.S. Ser. No. 10/185,994, filed concurrently herewith, entitled "Dimeric Azo Pyridone Colorants," with the named inventors Rina Carlini, Jeffery H. Banning, James M. Duff, Bo Wu, and James D. Mayo, the disclosure of which is totally incorporated herein by reference, discloses compounds of the formula

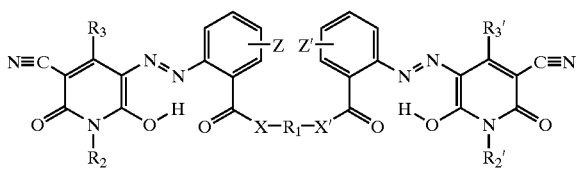

The compounds are useful as colorants, particularly in applications such as phase change inks.

Copending application U.S. Ser. No. 10/184,269, filed concurrently herewith, entitled "Phase Change Inks Containing Dimeric Azo Pyridone Colorants," with the named inventors Bo Wu, Rina Carlini, Jeffery H. Banning, James M. Duff, James D. Mayo, Jule W. Thomas, Paul F. Smith, and Michael B. Meinhardt, the disclosure of which is totally incorporated herein by reference, discloses a phase change ink composition comprising a phase change ink carrier and a colorant compound of the formula

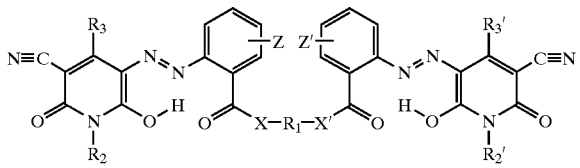

Copending application U.S. Ser. No. 10/185,264, filed concurrently herewith, entitled "Phase Change Inks Containing Azo Pyridone Colorants" with the named inventors Jeffery H. Banning, Bo Wu, James D. Mayo, James M. Duff, Rina Carlini, Jule W. Thomas, and Paul F. Smith, the disclosure of which is totally incorporated herein by reference, discloses a phase change ink composition comprising a phase change ink carrier and a colorant compound of the formula

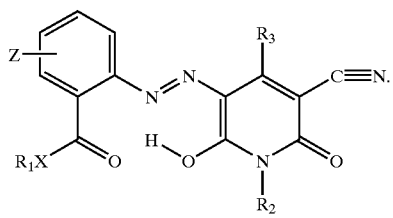

Copending application U.S. Serial No. 10/186,024, filed concurrently herewith, entitled "Azo Pyridone Colorants," with the named inventors Jeffery H. Banning, Rina Carlini, James D. Mayo, James M. Duff, and C. Wayne Jaeger, the disclosure of which is totally incorporated herein by reference, discloses compounds of the formula

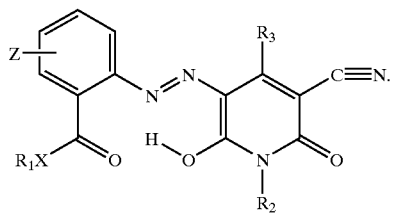

The compounds are useful as colorants, particularly in applications such as phase change inks.

Copending application U.S. Ser. No. 10/185,597, filed concurrently herewith, entitled "Process for Preparing Substituted Pyridone Compounds," with the named inventors James D. Mayo, James M. Duff, Rina Carlini, Roger E. Gaynor, and George Liebermann, the disclosure of which is totally incorporated herein by reference, discloses a process for preparing substituted pyridone compounds which comprises (a) admixing in the absence of a solvent (1) an amine of the formula $R_1$—$NH_2$ wherein $R_1$ is an alkyl group, an aryl group, an arylalkyl group, or an alkylaryl group, and (2) a first ester of the formula

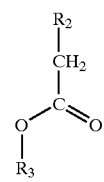

wherein $R_2$ is an electron withdrawing group and $R_3$ is an alkyl group; (b) heating the mixture containing the amine and the first ester to form an intermediate compound of the formula

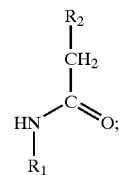

(c) admixing the intermediate compound with (1) a base and (2) a second ester of the formula

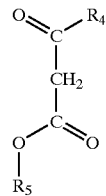

wherein $R_4$ is an alkyl group, an aryl group, an arylalkyl group, or an alkylaryl group and $R_5$ is an alkyl group, said second ester being present in a molar excess relative to the intermediate compound, said base being present in a molar excess relative to the intermediate compound, and (d) heating the mixture containing the intermediate compound, the second ester, and the base to form a pyridone compound of the formula

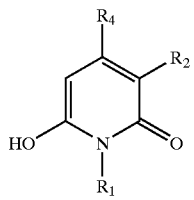

or a salt thereof. Also disclosed is a process for preparing diazopyridone colorants which comprises preparing a pyridone compound by the above process and reacting the pyridone compound with a diozonium salt to form a diazopyridone compound.

Copending application U.S. Ser. No. 10/185,828, filed concurrently herewith, entitled "Method for Making Dimeric Azo Pyridone Colorants," with the named inventors Rina Carlini, James D. Mayo, James M. Duff, Jeffery H. Banning, Paul F. Smith, George Liebermann, and Roger E. Gaynor, the disclosure of which is totally incorporated herein by reference, discloses a process for preparing a diazopyridone compound which comprises (a) preparing a first solution comprising (1) either (A) a dianiline of the

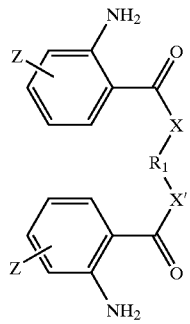

or (B) an aniline of the formula

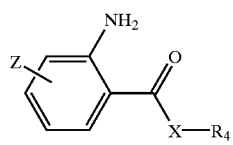

and (2) a first solvent mixture comprising (I) a solvent, (II) acetic acid, and (III) an optional second acid, said acetic acid being present in the solvent mixture in an amount of at least about 95 percent by weight of the solvent mixture, said first solution being at a temperature of about +15° C. or lower; (b) adding to the first solution nitrosylsulfuric acid, thereby forming a diazonium salt either (A) of the formula

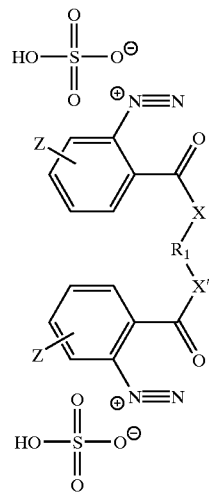

or (B) of the formula

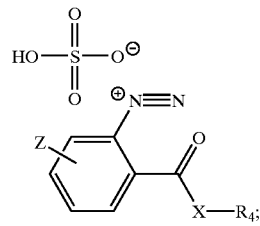

(c) preparing a second solution comprising (1) a second solvent mixture comprising water and an organic solvent soluble in or miscible in water, (2) either (A) a pyridone of the formula

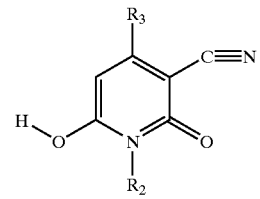

or (B) a dipyridone of the formula

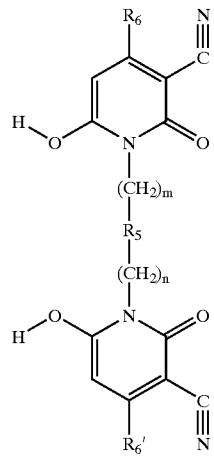

(3) a base present in an amount of at least about 3 molar equivalents of base per mole of pyridone moiety, and (4) an optional buffer salt, and (d) combining either (A) the second solution containing the dianiline and the first solution containing the pyridone, or (B) the second solution containing the aniline and the first solution containing the dipyridone to form a third solution and effect a coupling reaction to form a diazopyridone compound either (A) of the formula

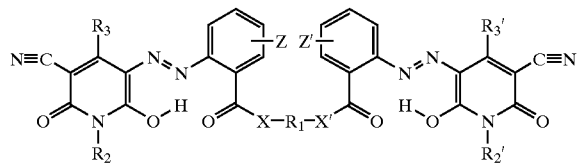

or (B) of the formula

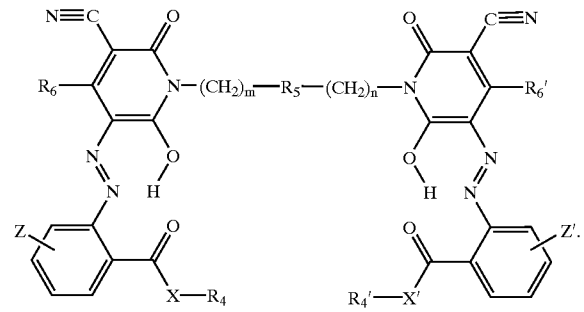

Copending application U.S. Ser. No. 10/186,023, filed concurrently herewith, entitled "Dimeric Azo Pyridone Colorants," with the named inventors Rina Carlini, James M. Duff, Jeffery H. Banning, Bo Wu, and James D. Mayo, the disclosure of which is totally incorporated herein by reference, discloses compounds of the formula.

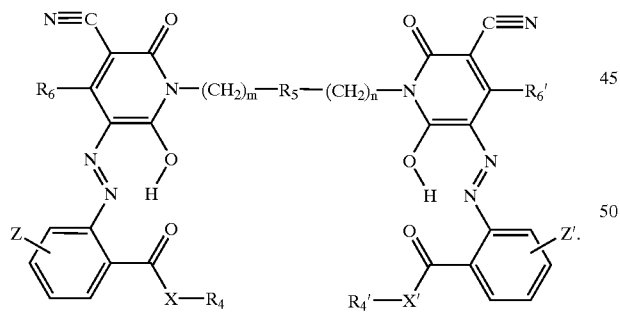

The compounds are useful as colorants, particularly in applications such as phase change inks.

Copending application U.S. Ser. No. 10/184,266, filed concurrently herewith, entitled "Phase Change Inks Containing Dimeric Azo Pyridone Colorants," with the named inventors Bo Wu, Rina Carlini, James M. Duff, Jeffery H. Banning, and James D. Mayo, the disclosure of which is totally incorporated herein by reference, discloses a phase change ink composition comprising a phase change ink carrier and a colorant compound of the formula

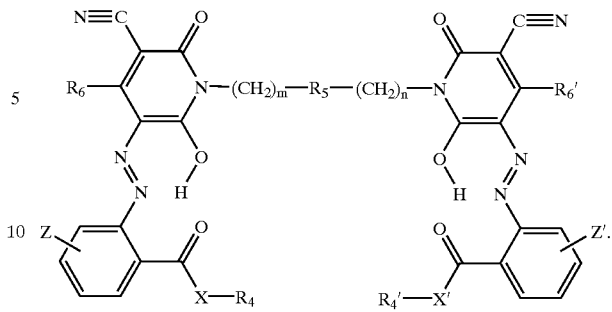

BACKGROUND OF THE INVENTION

The present invention is directed to a process for preparing dianthranilate compounds. More specifically, the present invention is directed to a process for preparing dianthranilate compounds containing relatively large hydrocarbon moieties, and to processes for preparing diazopyridone colorants with these dianthranilate compounds. One embodiment of the present invention is directed to a process for preparing dianthranilate compounds which comprises (a) admixing (1) a diol of the formula $R_1(OH)_2$, wherein $R_1$ is an alkylene group having at least about 20 carbon atoms, and wherein the —OH groups are primary or secondary, (2) isatoic anhydride, present in an amount of at least about 2 moles of isatoic anhydride per every one mole of diol, (3) a catalyst which is 1,4-diazabicyclo[2.2.2]octane, N,N,N',N'-tetramethylethylene diamine, or a mixture thereof, said catalyst being present in an amount of at least about 0.2 mole of catalyst per every one mole of diol, and (4) a solvent; and (b) heating the mixture thus formed to form a dianthranilate compound of the formula

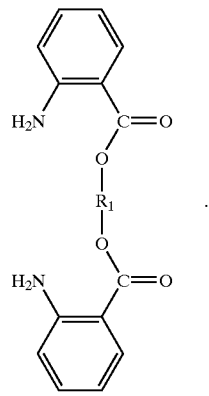

Another embodiment of the present invention is directed to a process for preparing a diazopyridone colorant which comprises (I) preparing a dianthranilate compound by (a) admixing (1) a diol of the formula $R_1(OH)_2$, wherein $R_1$ is an alkylene group having at least about 20 carbon atoms, and wherein the —OH groups are primary or secondary, (2) isatoic anhydride, present in an amount of at least about 2 moles of isatoic anhydride per every one mole of diol, (3) a catalyst which is 1,4-diazabicyclo[2.2.2]octane, N,N,N',N'-tetramethylethylene diamine, or a mixture thereof, said catalyst being present in an amount of at least about 0.2 mole of catalyst per every one mole of dial, and (4) a solvent; and (b) heating the mixture thus formed to form a dianthranilate compound of the formula

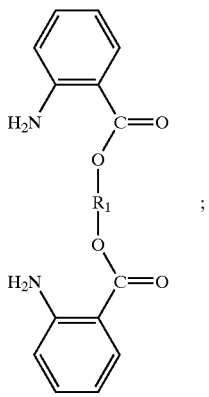

(II) reacting the dianthranilate compound with nitrosylsulfuric acid to form a diazonium salt of the formula

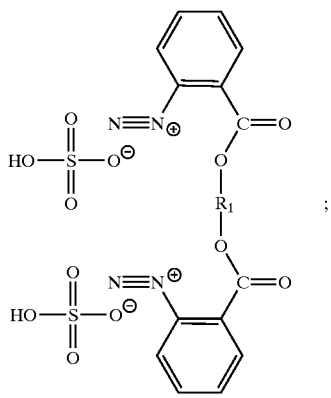

and (III) reacting the diazonium salt with a pyridone compound of the formula

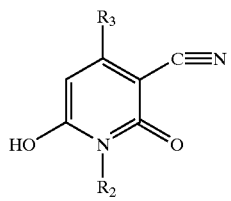

wherein $R_2$ is (i) an alkyl group, (ii) an aryl group, (iii) an arylalkyl group, (iv) an alkylaryl group, (v) an alkoxy group, (vi) an aryloxy group, (vii) an arylalkyloxy group, (viii) an alkylaryloxy group, (ix) a polyalkyleneoxy group, (x) a polyaryleneoxy group, (xi) a polyarylalkyleneoxy group, (xii) a polyalkylaryleneoxy group, (xiii) a heterocyclic group, (xiv) a silyl group, (xv) a siloxane group, (xvi) a polysilylene group, (xvii) a polysiloxane group, or (xviii) a group of the formula

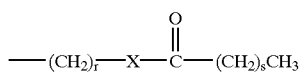

wherein r and s are each, independently of the other, integers representing a number of repeat —$CH_2$— groups, and $R_3$ is (i) an alkyl group, (ii) an aryl group, (iii) an arylalkyl group, or (iv) an alkylaryl group, to form a diazopyridone compound of the formula

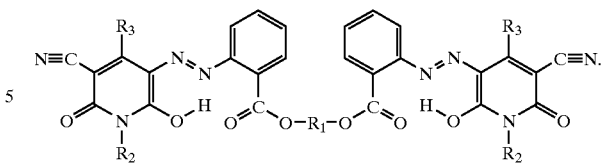

Methods for the preparation of simple anthranilate esters with isatoic anhydride and simple alcohols are known. These methods, however, when used to attempt to prepare anthranilate compounds from diols of relatively large hydrocarbons, exhibit disadvantages such as low yield and the production of undesirable intermediate products and byproducts. Moreover, known syntheses of dianthranilates have the added complication of entailing two consecutive additions of an intermediate, isatoic anhydride, to a diol, which can lead to contamination by a monoanthranilate mono alcohol if the reaction is not forced to completion. This monoanthranilate can be difficult to remove from the dianthranilate. Dianthranilates containing relatively large hydrocarbon moieties can be used to prepare specific diazopyridone colorants.

U.S. Pat. No. 3,929,863 (Blahak et al.) and German Patent Publication DE 2 040 644, the disclosures of each of which are totally incorporated herein by reference, disclose aromatic diamines having the general formula

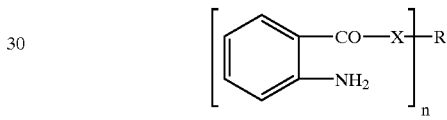

wherein n is an integer of from 2 to 8, X is sulfur or oxygen, and R is an n-valent hydrocarbon radical which may be interrupted by O or S atoms and which is obtained by removing OH or SH groups from a polyol or polythiol having a molecular weight of less than 600 which are prepared by reacting a compound having the formula (HX)$_n$R where X, n, and R as defined above with about n-equivalents of an isatoic acid anhydride in the presence of a strong base. The aromatic diamines of the invention are particularly useful as the active hydrogen containing component for reaction with polyisocyanates in the preparation of synthetic resins by the isocyanate-polyaddition process.

German Patent Publication DE 2 902 740 and European Patent Publication EP 0 013 956, the disclosures of each of which are totally incorporated herein by reference, disclose a process for the preparation of bis-(aminobenzoic acid)-alkanediol diester by esterification of alkanediols, except those in which hydroxy groups are in 1.4 or 2.5-positions, which nitrobenzoic acids and subsequent catalytic reduction of the bis-(nitrobenzoic acid)-alkanediol diester compound in a polar organic solvent, this solvent being partly or homogeneously miscible with water in all proportions, characterized by that the esterification is carried out in the presence of an aromatic sulfonic acid as a catalyst and in the absence of a solvent and at a temperature between 150 and 175° C.

"Polyamines Containing Ester Groups as Structural Components in Polyurethane Chemistry, J. Blahak et al., Angew. Makromol. Chem. (1972), Vol. 26, pp. 29 to 45, the disclosure of which is totally incorporated herein by reference, discloses aromatic diamines containing ester groups, such as 4-chloro-3,5-diaminobenzoates and aminophenyl aminobenzoates, which were prepared and used as noncarcinogenic and nontoxic chain extenders for polyurethane elastomers, giving processing and mechanical properties similar to those obtained with 3,3'-dichloro-4,4'-diaminodiphenylmethane. Anthranilates of both high and low molecular weight polyols were also used, but were much less reactive than compounds with amino groups in the meta or para position.

"The Chemistry of Isatoic Anhydride," G. M. Coppola, *Synthesis*, p. 505 (1980), the disclosure of which is totally incorporated herein by reference, discloses various reactions to synthesize isatoic anhydride and reactions of isatoic anhydride with various classes of compounds, including alcohols.

"Isatoic Anhydride. IV. Reactions with Various Nucleophiles," R. P. Staiger et al., *J. Org. Chem.*, Vol. 24, p. 1214 (1959), the disclosure of which is totally incorporated herein by reference, discloses reactions of isatoic anhydride with alcohols, mercaptans, and compounds with active methylene groups forming substituted esters, thio esters, carbamates, and substituted quinolines. A mechanism for the alternate cleavage of the anhydride ring is elucidated.

European Patent Publication 1 125 990 and PCT Patent Publication WO 01/09256, the disclosures of each of which are totally incorporated herein by reference, discloses an aqueous ink for ink jet recording which contains at least a water-insoluble coloring matter, water, and a resin as main components and which takes the form of an emulsion, which is characterized by containing at least one yellow hue coloring matter selected from the group consisting of a quinophthalone compound represented by the formula (1)

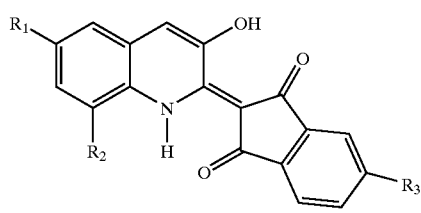

(1)

wherein each of $R_1$ to $R_3$ independently represents a hydrogen atom, an unsubstituted or substituted alkyl group, —$CONR_4R_5$, or —$COOR_6$ (in which each of $R_4$ to $R_6$ independently represents a hydrogen atom, an unsubstituted or substituted alkyl group, or an unsubstituted or substituted aryl group) and all of $R_1$ to $R_3$ are not a hydrogen atom at the same time, and a pyridone azo compound represented by the formula (2)

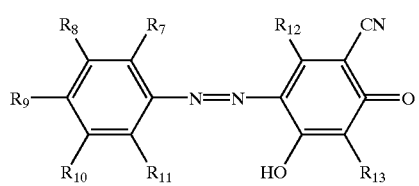

(2)

wherein each of $R_7$ to $R_{11}$ independently represents a hydrogen atom, a halogen atom, an unsubstituted or substituted alkyl group, an aralkyl group, an unsubstituted or substituted alkoxy group, an unsubstituted or substituted aryl group, an unsubstituted or substituted aryloxy group, a hydroxyl group, —$NR_{14}R_{15}$ (in which $R_{14}$ and $R_{15}$ independently represent a hydrogen atom, an unsubstituted or substituted alkyl group, or an aralkyl group), —$COX_1$ (in which $X_1$ represents an unsubstituted or substituted alkoxy group, an unsubstituted or substituted aryloxy group, or —$NR_{16}R_{17}$ (in which each of $R_{16}$ and $R_{17}$ independently represent a hydrogen atom, an unsubstituted or substituted alkyl group, an aralkyl group, or an unsubstituted or substituted aryl group)), —$COO(CH_2)_n$—$COX_2$, —$OCOX_3$, or —$NHCOX_4$ (in which each of $X_2$ to $X_4$ independently represents an unsubstituted or substituted alkyl group, an aralkyl group, an unsubstituted or substituted aryl group, an unsubstituted or substituted alkoxy group, or an unsubstituted or substituted aryloxy group, and n is an integer of 1 to 3), $R_{12}$ represents an unsubstituted or substituted alkyl group, and $R_{13}$ represents' an unsubstituted or substituted alkyl group, an aralkyl group, or an unsubstituted or substituted aryl group. The ink is for ink jet recording having excellent light resistance and storage stability, and enables formation of a high quality image without blotting, and the obtained recording image is excellent in water resistance.

PCT Patent Publication WO 01/21714, the disclosure of which is totally incorporated herein by reference, discloses compositions comprising a solvent and at least one compound of the

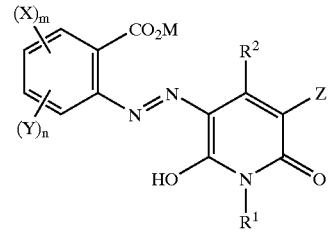

in which $R_1$ represents H, an optionally substituted $C_{1-8}$ carbyl derived group, or a group of the formula

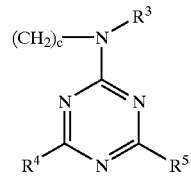

where C is from 2 to 6, $R^3$ represents optionally substituted $C_{1-8}$ carbyl derived group, $R^4$ and $R^5$ independently represent an optional substituent, $R^2$ represents an optionally substituted $C_{1-8}$ carbyl derived group, X Y, and Z independently represent H or an optional substituent, M represents H or a cation, and m and n independently represent 0,1, or 2. Also disclosed are compounds of the above formula providing that at least one of $R^1$, $R^2$, X, Y, or Z comprises a group of formula $SO_3M$ or $PO_3M_2$. These compositions and compounds are useful as the colorants to prepare color filters for displays.

U.S. Pat. No. 4,247,456 (von Brachel et al.), the disclosure of which is totally incorporated herein by reference, discloses water-insoluble monoazo dyes of the formula

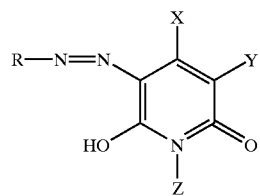

wherein R is the residue of a benzene, naphthalene, diphenyl, diphenylmethane, or heterocyclic diazo compound which is free from water solubilizing groups, produced by reacting a diazotized amine of the benzene, naphthalene, diphenyl, diphenylmethane, or heterocyclic series which is free from water solubilizing groups with the appropriate 6-hydroxy-2-pyridone and the utility thereof for the dyeing and printing of synthetic fabric materials to yellow to red shades having excellent fastness to light and sublimation.

U.S. Pat. No. 3,957,749 (von Brachel et al.), the disclosure of which is totally incorporated herein by reference, discloses water-insoluble monoazo dyes of the formula

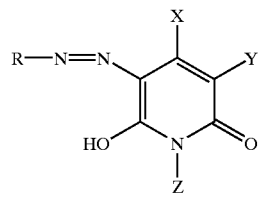

produced by reacting a diazotized amine of the benzene, naphthalene, diphenyl, diphenylmethane, or heterocyclic series which is free from water solubilizing groups with the appropriate 6-hydroxy-2-pyridone and the utility thereof for the dyeing and printing of synthetic fabric materials to yellow to red shades having excellent fastness to light and sublimation.

Japanese Patent Publication JP 05331382, the disclosure of which is totally incorporated herein by reference, discloses a specific pyridone azo pigment which is bright yellow and highly soluble in a solvent, absorbs light of long wavelength, and is useful for a thermal transfer sheet. The pyridone azo pigment is represented by the formula

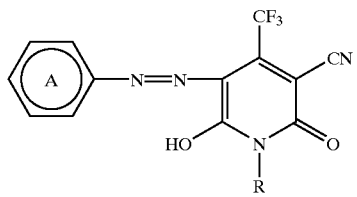

wherein R is H, alkyl, substituted alkyl, cycloalkyl, aryl, or optionally substituted phenyl, and ring A is a benzene ring optionally having a nonionic group. The pigment is prepared by diazotizing an aniline compound and coupling the resulting diazo compound with a pyridone compound. Having a good solubility in an organic solvent and a good dispersibility in water, the pigment facilitates the preparation of an ink containing a high concentration of the pigment homogeneously dissolved or dispersed. The prepared ink enables the preparation of a thermal transfer sheet coated with the ink uniformly in a high density.

British Patent 1,559,001 (Harvey et al.), the disclosure of which is totally incorporated herein by reference, discloses a hydrophilic textile material colored with a dyestuff of the formula

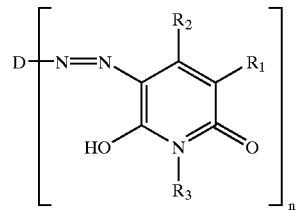

wherein D is the residue of a diazo or tetrazo component; $R_1$ is a hydrogen atom or an alkyl, chloro, acetamido, benzamido, carbamoyl, or an N-substituted carbamyl, for example —CONHBr, group or, preferably, a cyano group; $R_2$ is an alkyl group, especially methyl, optionally substituted with a chlorine atom, a phenyl group, optionally substituted with an alkyl or alkoxy group, or a carboxylic acid or carboxylic acid ester group; or $R_1$ and $R_2$ together with the carbon atoms in the 3- or 4-position of the pyridone ring may form an alicyclic or aromatic ring system so that, for example, $R_1$ and $R_2$ together may be a tri- or tetramethylene group forming with the pyridone of penteno [c] or hexeno [c] pyrid-2-one, or $R_1$ and $R_2$ may form together with the adjacent carbon atoms of the pyridone ring a benzene ring giving a benz [c] pyrid-2one; $R_3$ is an aryl group carrying one or more substituents selected from —NO, —SO$_2$R$^1$, —COR$^1$, —COOR$^1$, —CF, or —CN, wherein $R^1$ is an optionally substituted alkyl or aryl group; and n is an integer which may be 1 or 2.

German Patent Publication DE 19646430, the disclosure of which is totally incorporated herein by reference, discloses dye mixtures comprising at least two structurally different dyes, each corresponding to formula

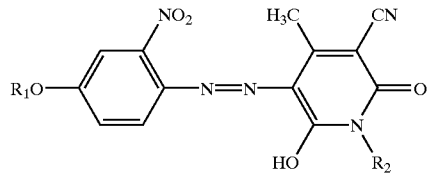

wherein $R_1$ is $C_1$–$C_4$ alkyl; $R_2$ is the $(CH_2)_nO$—$R_5$ radical; $R_5$ is, independently of $R_1$, $C_1$–$C_4$ alkyl or phenyl (which is unsubstituted or substituted by $C_1$–$C_4$ alkyl, $C_1$–$C_4$ alkoxy, hydroxy, or halogen); and n is 2 or 3, which dye mixtures are suitable for dyeing or printing textile fibre materials (e.g. polyester materials), giving dyeings having good around fastness properties.

German Patent Publication DE 19646429, the disclosure of which is totally incorporated herein by reference, discloses dye mixtures comprising at least two structurally different dyes, each of which has the formula

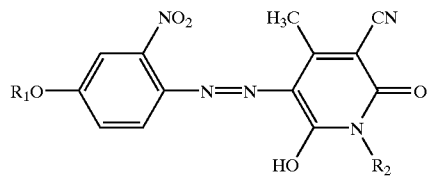

in which $R_1$ is $C_1$–$C_4$ alkyl and $R_2$ is isopropyl, n-butyl, isobutyl, sec-butyl, or tert-butyl; or $C_1$–$C_3$ alkyl which is substituted by phenyl or phenoxy; or $R_1$ is phenyl (which is unsubstituted or substituted by $C_1$–$C_4$ alkyl, $C_1$–$C_4$ alkoxy, hydroxyl, or halogen), $C_1$–$C_4$ alkoxy-$C_1C_3$ alkylene, phenoxy-$C_1$–$C_3$ alkylene, or $C_1$–$C_3$ alkyl which is substituted by phenyl (which is unsubstituted or substituted by $C_1$–$C_4$ alkyl, $C_1$–$C_4$ alkoxy, hydroxyl, or halogen) and $R_2$ is $C_1$–$C_{10}$ alkyl (which is unsubstituted or substituted by hydroxyl, $OCOR_3$, or phenoxy, where the phenyl ring in phenoxy is unsubstituted or substituted by $C_1$–$C_4$ alkyl, $C_1$–$C_4$ alkoxy, hydroxyl, or halogen) and the alkyl chain in $C_1$–$C_4$ alkyl from $C_2$ can be interrupted by one or more oxygen atoms; phenyl (which is unsubstituted or substituted by $C_1$–$C_4$ alkyl, $C_1$–$C_4$ alkoxy, hydroxyl, or halogen); or $C_5$–$C_7$ cycloalkyl; and $R_3$ is $C_1$–$C_4$ alkyl, are suitable for dyeing or printing textile fibre materials (e.g. polyester materials) and give dyeings with good allround properties.

German Patent Publication DE 19647869, the disclosure of which is totally incorporated herein by reference, discloses a dye mixture containing at least 2 dyes with different structures, each of formula

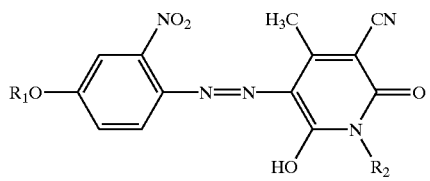

where $R_1$ is a 1–4C alkyl; and $R_2$ is a linear 1–3C alkyl. Also claimed is hydrophobic fibre material, preferably polyester textile material, dyed or printed with the mixture.

PCT Patent Publication WO 99/43754, the disclosure of which is totally incorporated herein by reference, discloses compounds of the formula

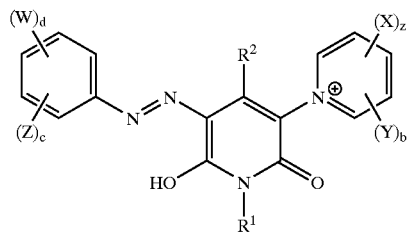

and salts and toutomers thereof, wherein: $R_1$ and $R_2$ each independently is H, optionally substituted alkyl, optionally substituted aryl, or optionally substituted arylalkyl; each W and each X independently is —COOH, —$SO_3H$, —$PO_3H_2$, or alkyl substituted by one or more groups selected from —COOH, —$SO_3H$, and —$PO_3H_2$; each Y and each Z independently is a substituent other than those defined for W and X; a and d each independently is 1 to 5; b and c each independently is 0 to 4; (a+b) has a value of 5 or less; and (c+d) has a value of 5 or less. Also claimed are inks containing a compound of this formula, an ink jet printing process using the inks, substrates printed with the inks, and ink jet printer cartridges containing the inks.

U.S. Pat. No. 5,929,218 (Lee et al.), the disclosure of which is totally incorporated herein by reference, discloses pyridone-based yellow monoazo dyes used in thermal transfer having following formula which have good stability and hue

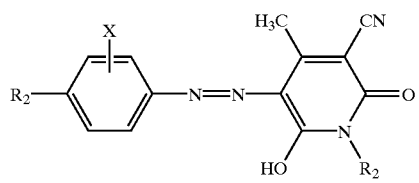

wherein $R_1$ is hydrogen atom; unsubstituted or substituted alkyl group of from 1 to 8 carbon atoms with alkoxy or aryl; or unsubstituted or substituted aryl group with alkoxy or halogen, and X is hydrogen atom; alkyl group of from 1 to 4 carbon atoms; alkoxy group; or halogen; $R_2$ is selected from the following groups;

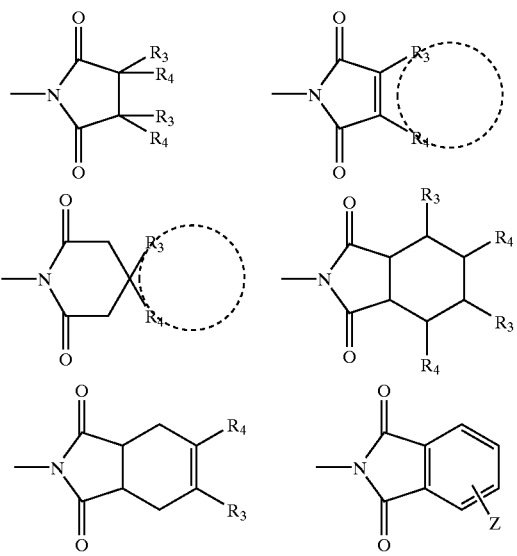

wherein $R_3$ and $R_4$ are independently selected from groups consisting hydrogen, substituted or unsubstituted alkyl group of from 1 to 4 carbon atoms, halogen, alkyl carboxylate, and carbonyl group: $R_3$–$R_4$ is noncyclization with $R_3$ and $R_4$ and selected respectively from the above substituents ($R_3$ and $R_4$) or saturated or unsaturated cycloalkyl of from 3 to 6 carbon atoms, Z is nitro, halogen, alkyl group of from 1 to 4 carbon atoms, alkoxy, sulfonyl, carbonyl, carboxyamide, sulfonamino, cyano, hydroxy, or hydrogen atom.

European Patent Publication EP 0 706 679 B1, U.S. Pat. No. 5,853,929 (Campbell), and PCT Patent Publication WO 95/00885, the disclosures of each of which are totally incorporated herein by reference, disclose colored cyan toner for electroreprography and laser printing based on Solvent Blue 70, and a trichomatic set of coloured toners based on Solvent Blue 70, benzodifuranone red dyes, and azo pyridone yellow dyes of the formula

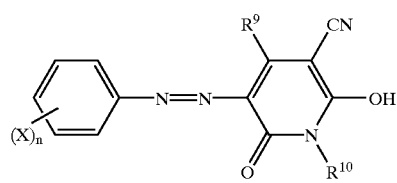

wherein X is halogen, nitro, or a group —$COOR^5$, $R^9$ is $C_{1-12}$ alkyl, $R^5$ is $C_{1-8}$ alkyl or a group of formula —($C_1$-

3-alkylene)-(CO)$_q$—Z wherein q is 0 or 1 and Z is —OR$^6$ or —NR$^6$R$^7$ when q=1 or Z is —OR$^8$ when q=0, R$^6$ is selected from optionally substituted C$_{1-8}$ alkyl, optionally substituted C$_{1-8}$ alkoxy-C$_{1-8}$ alkyl, and a second group represented by R$^5$ in which R$^6$ is optionally substituted C$_{1-8}$ alkyl or optionally substituted C$_{1-8}$ alkoxy-C$_{1-8}$ alkyl, R$^7$ is selected from H and optionally substituted C$_{1-8}$ alkyl, and R$^8$ is selected from optionally substituted C$_{1-8}$ alkyl, optionally substituted C$_{1-8}$ alkoxy-C$_{1-8}$ alkyl, optionally substituted C$_{1-8}$ alkyl sulfonyl or carbonyl, and optionally substituted phenyl sulfonyl or carbamoyl.

European Patent Publication EP 0 247 737, the disclosure of which is totally incorporated herein by reference, discloses a thermal transfer printing sheet suitable for use in a thermal transfer printing process, especially for the conversion of a digital image into a visible print, comprising a substrate having a coating comprising a dye of the formula

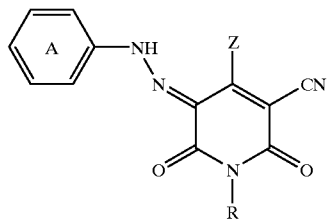

wherein Ring A is unsubstituted or carries, in the 2- or 4-position with respect to the azo link, at least one group selected from —CX$_3$, X$^1$, CN, NO$_2$, —OCO.Y, —CO.Y, —CO.H, —OS$_2$.Y, and —SOO$_2$. Y, provided that A is substituted when Z is CH$_3$ and R is C$_{2-4}$-alkyl; X and X$^1$ are each independently halogen; Y is selected from R$^1$, —OR$^1$, SR$^1$, and —NR$^1$R$^2$; R$^1$ is selected from C$_{1-12}$-alkyl, C$_{1-12}$-alkyl interrupted by one or two groups selected from —O—, —CO—, O.CO—, and —CO.O—, C$_{3-7}$-cycloalkyl, mono- or bi-cyclic aryl, and C$_{1-3}$-alkylene attached to an adjacent carbon atom on Ring A; R$^2$ is selected from H, C$_{1-12}$-alkyl, C$_{3-7}$-cycloalkyl, and mono-or bi-cyclic aryl; Z is C$_{1-12}$-alkyl or phenyl; and R is selected from C$_{2-12}$-alkyl unbranched in the alpha-position, C$_{2-12}$-alkyl unbranched in alpha-position and interrupted by one or two groups selected from —O—, —CO—, O.CO—, and —CO.O—, phenyl, C$_{1-4}$-alkylphenyl, biphenyl, and biphenyl interrupted by a group selected from —O—, —CO—, O.CO—, and —CO.O—, each of which is free from hydrogen atoms capable of intermolecular hydrogen bonding.

U.S. Pat. No. 5,041,413 (Evans et al.), the disclosure of which is totally incorporated herein by reference, discloses a yellow dye-donor element for thermal dye transfer comprises a support having thereon a dye layer comprising a mixture of yellow dyes dispersed in a polymeric binder, at least one of the yellow dyes having the formula

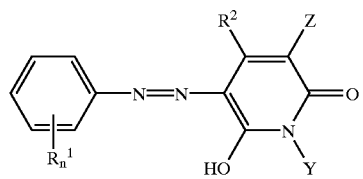

wherein: each R$^1$ independently represents a substituted or unsubstituted alkyl group of from 1 to about 10 carbon atoms, a cycloalkyl group of from about 5 to about 7 carbon atoms; a substituted or unsubstituted allyl group; an aryl group of from about 6 to about 10 carbon atoms; a hetaryl group of from 5 to 10 atoms; acyl; arylsulfonyl; aminocarbonyl; aminosulfonyl; fluorosulfonyl; halogen; nitro; alkylthio; or arylthio; or any two adjacent R$^1$'s together represent the atoms necessary to form a 5- or 6-membered fused ring; n represents an integer from 0–4; R$^2$ represents hydrogen; a substituted or unsubstituted alkyl, cycloalkyl, allyl, aryl or hetaryl group as described above for R$_1$; cyano; acyl; alkylsulfonyl; arylsulfonyl; or alkoxycarbonyl; Z represents cyano; alkoxycarbonyl; acyl; nitro; arylsulfonyl or alkylsulfonyl; Y represents hydrogen; a substituted or unsubstituted alkyl, cycloalkyl, allyl, aryl or hetaryl group as described above for R$^1$; amino; alkylamino; arylamino; acylamino; or sulfonylamino; and at least one of the other of the dyes having the formula

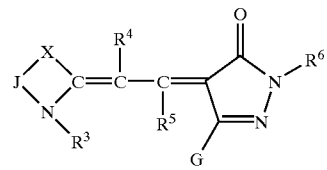

wherein R$^3$ represents the same groups as R$^1$ above; R$^4$ and R$^5$ each independently represents hydrogen, R$^3$; cyano; acyloxy; alkoxy of 1 to about 6 carbon atoms; halogen; or alkoxycarbonyl; or any two of R$^3$, R$^4$ and R$^5$ together represent the atoms necessary to complete a 5- to 7-membered ring; R$^6$ represents the same groups as R$^3$; G represents a substituted or unsubstituted alkyl, cycloalkyl or allyl group as described above for R$^3$, NR$^7$R$^8$ or OR$^9$; R$^7$ and R$^8$ each independently represents hydrogen, acyl or R$^3$, with the proviso that R$^7$ and R$^8$ cannot both be hydrogen at the same time; or R$^7$ and R$^8$ together represent the atoms necessary to complete a 5- to 7-membered ring; R$^9$ represents the same groups as R$^3$; X represents C(R$^{10}$)(R$^{11}$), S, O or NR$^{10}$; R$^{10}$ and R$^{11}$ each independently represents the same groups as R$^3$; or R$^{10}$ and R$^{11}$ together represent the atoms necessary to complete a 5- to 7-membered ring; and J represents the atoms necessary to complete a 5- or 6-membered ring which may be fused to another ring system.

U.S. Pat. No. 4,359,418 (Lienhard et al.), the disclosure of which is totally incorporated herein by reference, discloses azo dyestuff sulfonic acid salts of the formula

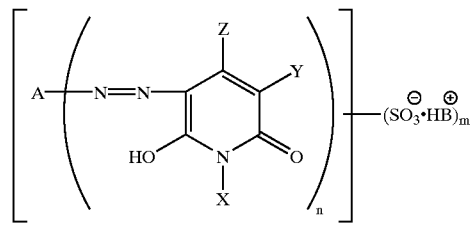

wherein A represents a carbocyclic or heterocyclic aromatic radical, B represents an aliphatic, cycloaliphatic or araliphatic amine, X represents a hydrogen atom or a substituted or unsubstituted alkyl group, a cycloalkyl, aralkyl or aryl group, Y represents a hydrogen or halogen atom, a nitro, cyano, acyl, sulfonic acid, arylsulfonyl, alkoxycarbonyl group or a substituted or unsubstituted alkyl, sulfamoyl or carbamoyl group, Z represents a substituted or unsubstituted alkyl group or an aryl radical, m and n are 1 or 2; said dyestuffs salts having good solubility in organic solvents and functioning to color solutions of film forming polymers in yellow to orange shades.

German Patent Publication DE 3538517 and U.S. Pat. No. 5,037,964 (Moser et al.), the disclosures of each of which are totally incorporated herein by reference, disclose sulfonic acid group-free basic azo compounds, which correspond in one of the possible tautomeric forms to the formula

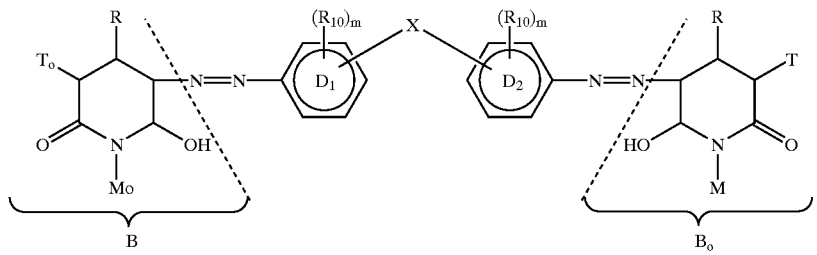

their preparation and their use for dyeing paper.

Japanese Patent Publication JP 03192158, the disclosure of which is totally incorporated herein by reference, discloses obtaining a yellow dye exhibiting high dyeing speed and degree of exhaustion in dyeing a textile material, leather, pulp, paper, etc., as well as excellent brightness and fastness to water by selecting a compound wherein a pyridopyridinium salt is linked to diphenylfluorene through azo groups. A cationic compound of the formula

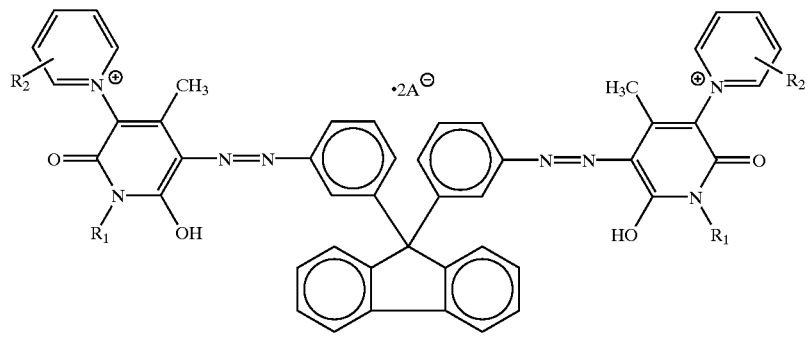

wherein $R_1$ is H or 1–4C alkyl; $R_2$ is H, 1–4C alkyl, or alkoxy; and $A^-$ is an anion which has a structure wherein a tetrazo compound, of 9,9'-bis(4-anilino) fluorene is coupled with a pyridone derivative yellow dye, which is useful for dyeing an unsized pulp or paper (e.g. a napkin, table cloth, or sanitary paper). The dyeing with the dye is carried out at a pH of 4–8, preferably 5–7, and at 10–50° C., preferably 15–30° C.

British Patent Publication GB 2 008 606, the disclosure of which is totally incorporated herein by reference, discloses water-insoluble yellow monoazo dyes suitable for dyeing hydrophobic synthetic fibres, particularly polyesters, having the formula

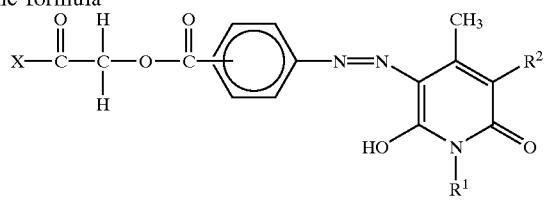

in which X represents $OR^3$ or $NHR^3$, $NR^3R^4$ ($R^3$, $R^4$ together optionally forming with N a ring having 5 to 6 carbon atoms, $NHR^5$; $R^1$ represents a hydrogen atom, an alkyl having 1 to 5 carbon atoms, $(CH_2)_2OH$ or $(CH_2)_3OR^3$; $R^2$ represents CN, $COOR^3$, $CONHR^3$, $CONR^3R^4$ ($R^3$, $R^4$ together optionally forming with N a ring having 5 to 6 carbon atoms); $R^3$ and $R^4$ represent alkyl groups having 1 to 5 carbon atoms; and $R^5$ represents a cycloalkyl having 5 or 6 carbon atoms. The dyes may be prepared by the reaction of

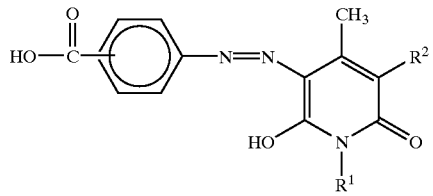

with Hal-$CH_2$ —CO—X in which Hal represents Cl or Br.

"Preparation and Evaluation of Yellow Pigments Based on H-Pyridone and Esters of Aminoterephthalic Acid," P. Slosar et al., CHEMagazin, Vol. 9, No. 6, pp. 8–11 (1999), the disclosure of which is totally incorporated herein by reference, discloses yellow pigments based on H-pyridone and esters of aminoterephthalic acid wherein the color strength, brilliance (purity), and deepening of greenish shade were the larger the smaller alkyl is in the carbalkoxy group in o-position towards the azo group and the greater alkyl is in the carbalkoxy group in m-position towards the azo group.

Of potential background interest with respect to the present invention are the following references: U.S. Pat. No. 5,919,839; U.S. Pat. No. 5,827,918; U.S. Pat. No. 4,889,560; U.S. Pat. No. 5,372,852; "Synthesis, Morphology, and Optical Properties of Tetrahedral Oligo(phenylenevinylene) Materials," S. Wang et al., J. Am. Chem. Soc., Vol. 120, p. 5695 (2000); "Syntheses of Amphiphilic Diblock Copolymers Containing a Conjugated Block and Their Self-Assembling Properties," H. Wang et al., J. Am. Chem. Soc., Vol. 122, p. 6855 (2000); "Crystal Engineering of Conjugated Oligomers and the Spectral Signature of π Stacking in Conjugated Oligomers and Polymers," A. Koren et al., Chem. Mater., Vol. 12, p. 1519 (2000); "Investigation of the Reaction Conditions for the Synthesis of 4,6-Disubstituted-3-cyano-2-pyridones and 4-Methyl-3-cyano-6-hydroxy-2-pyridone," D. Z. Mijin et al., J. Serb. Chem. Soc., Vol. 59, No. 12, p. 959 (1994); "Synthesis of Isoquinoline Alkaloids. II. The Synthesis and Reactions of 4-Methyl-3-pyridinecarboxaldehyde and Other 4-Methyl-3-substituted Pyridines, J. M. Bobbitt et al., *J. Org. Chem.*, Vol 25, p. 560 (1960); "Synthesis and Dyeing Characteristics of 5-(4-Arylazophenyl) azo-3-cyano-4-methyl-6-hydroxy-2-pyridones," J. Kanhere et al., *Indian Journal of Textile Research*, Vol. 13, p. 213 (1988); "Synthesis of Some Pyridone Azo Dyes from 1 Substituted 2-Hydroxy-6-pyridone Derivatives and their Colour Assessment," C. Chen et al., *Dyes and Pigments*, Vol. 15, p. 69- (1991); German Patent Publication DE 3543360; Japanese Patent Publication JP 2001214083; German Patent Publication DE 3505899; Indian Patent Publication 147527; European Patent Publication EP 0 524 637; European Patent Publication EP 0 529 282; European Patent Publication EP 0 083 553; Japanese Patent Publication JP 2000 62327; Japanese Patent Publication JP 85152563; "Synthesis of 3 Cyano-6-hydroxy-5-(2-(perfluoroalkyl)phenylazo)-2-pyridones and their Application for Dye Diffusion Thermal Transfer Printing," *Bull. Chem. Soc. Jpn.*, 1993, Vol. 66, Iss. 6, Pp.1790–4; European Patent Publication 0 844 287; European Patent Publication 0 404 493; U.S. Pat. No. 5,902,841, U.S. Pat. No. 5,621,022; U.S. Pat. No. 5,006,170; Chinese Patent Publication CN 1115773; German Patent Publication DE 3447117; Japanese Patent Publication JP 5331382; Japanese Patent Publication JP 63210169; Japanese Patent Publication JP 63199764; Japanese Patent Publication JP 63199763; Japanese Patent Publication JP 63199762; Japanese Patent Publication JP 63199761; Japanese Patent Publication JP 63199760; Japanese Patent Publication JP 63071392; Japanese Patent Publication JP 61181865; Japanese Patent Publication JP 61036366; Japanese Patent Publication JP 60152563; Japanese Patent Publication JP 60112862; Japanese Patent Publication JP 60112861; Japanese Patent Publication JP 58149953; Japanese Patent Publication JP 56092961; Japanese Patent Publication JP 56026957; Japanese Patent Publication JP 55099958; Japanese Patent Publication JP 96 11443 (JP8011443); Japanese Patent Publication JP 93169849 (JP5169849); Japanese Patent Publication JP 93 51536 (JP5051536); Japanese Patent Publication JP 90185569 (JP2185569); European Patent Publication 0 319 234; European Patent Publication 0 314 002; European Patent Publication 0302401; U.S. Pat. No. 4,734,349; Japanese Patent Publication JP 87290762 (JP62290762); Japanese Patent Publication JP 86244595 (JP61244595); Indian Patent Publication IN 147868; Spanish Patent Publication 475254 (Equivalent of Italian Patent Publication IT 1088895); German Patent Publication DE 2727809; "Colour and Constitution of Azo Dyes Derived from 2-Thioalkyl-4,6-Diaminopyrimidines and 3 Cyano-1,4-dimethyl-6-hydroxy-2Coupling Components," L. Cheng et al., *Dyes and Pigments*, Vol. 7, No. 5, pp. 373–388 (1986); European Patent Publication 1 168 046; U.S. Pat. No. 4,644,058; Japanese Patent Publication JP 63039380; Japanese Patent Publication JP 54102328, Japanese Patent Publication JP 54070337; "Trends in Modern Dye Chemistry. Part 10," N. R. Ayyangar and K. V. Srinivasan, Colourage, Vol. 37, No. 2, pp. 29–30 (Jan. 16, 1990); European Patent Publication EP 0 172 283; Japanese Patent Publication JP 05169854; Japanese Patent Publication JP 04292988; Japanese Patent Publication JP 63161060; Japanese Patent Publication JP 61244595; Korean Patent Publication KR 119563; European Patent Publication EP 0 142 863; European Patent Publication EP 0 023 770; Japanese Patent Publication JP 00239549 (JP2000239549); Japanese Patent Publication JP 11269402; Japanese Patent Publication JP 09041267; Japanese Patent Publication JP 08039941; U.S. Pat. No. 4,994,564; Japanese Patent Publication JP 06294909; Japanese Patent Publication JP 06122829; Japanese Patent Publication JP 05255602; Japanese Patent Publication JP 05051536; Japanese Patent Publication JP 04235093; European Patent Publication EP 0 468 647; European Patent Publication EP 0063275; U.S. Pat. No. 4,216,145; and German Patent Publication DE 2606506; the disclosures of each of which are totally incorporated herein by reference.

While known compositions and processes are suitable for their intended purposes, a need remains for improved methods for preparing dianthranilate compounds. In addition, a need remains for methods for preparing dianthranilate compounds containing relatively large hydrocarbon moieties. Further, a need remains for methods for preparing dianthranilate compounds containing relatively large hydrocarbon moieties that enable desirably high product yields. Additionally, a need remains for methods for preparing dianthranilate compounds containing relatively large hydrocarbon moieties that enable desirably high degrees of conversion of reactants to products. There is also a need for methods for preparing dianthranilate compounds containing relatively large hydrocarbon moieties that are environmentally safe. In addition, there is a need for methods for preparing dianthranilate compounds containing relatively large hydrocarbon moieties that are cost-effective. Further, there is a need for methods for preparing dianthranilate compounds containing relatively large hydrocarbon moieties that employ readily available starting materials. Additionally, there is a need for methods for preparing dianthranilate compounds containing relatively large hydrocarbon moieties that entail desirably simple processes. A need also remains for methods for preparing dianthranilate compounds containing relatively large hydrocarbon moieties that require desirably short periods of time. In addition, a need remains for methods for preparing dianthranilate compounds containing relatively large hydrocarbon moieties that afford dianthranilates uncontaminated with any monoanthranilate-mono alcohol (that otherwise might have been formed as an intermediate during the synthesis). Further, a need remains for methods for preparing dianthranilate compounds containing relatively large hydrocarbon moieties that afford the product in relatively high purity without the need for post-synthetic treatments such as recrystallization, distillation, or column chromatography. Additionally, a need remains for methods for preparing diazopyridone colorants that have the aforementioned advantages.

SUMMARY OF THE INVENTION

The present invention is directed to a process for preparing dianthranilate compounds which comprises (a) admixing (1) a diol of the formula $R_1(OH)_2$, wherein $R_1$ is an alkylene group having at least about 20 carbon atoms, and wherein the —OH groups are primary or secondary, (2) isatoic anhydride, present in an amount of at least about 2 moles of isatoic anhydride per every one mole of diol, (3) a catalyst which is 1,4-diazabicyclo[2.2.2]octane, N,N,N',N'-tetramethylethylene diamine, or a mixture thereof, said catalyst being present in an amount of at least about 0.2 mole of catalyst per every one mole of diol, and (4) a solvent; and (b) heating the mixture thus formed to form a dianthranilate compound of the formula

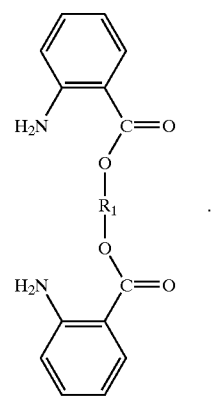

Another embodiment of the present invention is directed to a process for preparing a diazopyridone colorant which comprises (I) preparing a dianthranilate compound by (a) admixing (1) a diol of the formula $R_1(OH)_2$, wherein $R_1$ is an alkylene group having at least about 20 carbon atoms, and wherein the —OH groups are primary or secondary, (2) isatoic anhydride, present in an amount of at least about 2 moles of isatoic anhydride per every one mole of diol, (3) a catalyst which is 1,4-diazabicyclo [2.2.2]octane, N,N,N', N'-tetramethylethylene diamine, or a mixture thereof, said catalyst being present in an amount of at feast about 0.2 mole of catalyst per every one mole of diol, and (4) a solvent; and (b) heating the mixture thus formed to form a dianthranilate compound of the formula

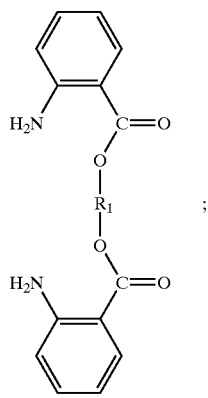

(II) reacting the dianthranilate compound with nitrosylsulfuric acid to form a diazonium salt of the formula

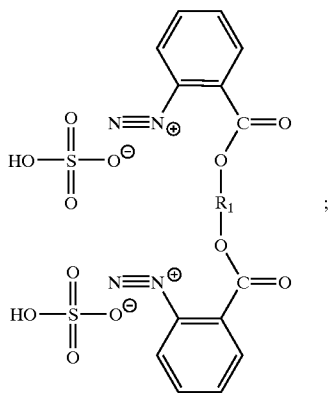

and (III) reacting the diazonium salt with a pyridone compound of the formula

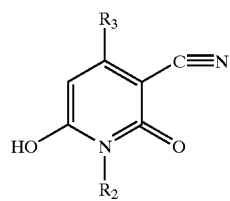

wherein $R_2$ is (i) an alkyl group, (ii) an aryl group, (iii) an arylalkyl group, (iv) an alkylaryl group, (v) an alkoxy group, (vi) an aryloxy group, (vii) an arylalkyloxy group, (viii) an alkylaryloxy group, (ix) a polyalkyleneoxy group, (x) a polyaryleneoxy group, (xi) a polyarylalkyleneoxy group, (xii) a polyalkylaryleneoxy group, (xiii) a heterocyclic group, (xiv) a silyl group, (xv) a siloxane group, (xvi) a polysilylene group, (xvii) a polysiloxane group, or (xviii) a group of the formula

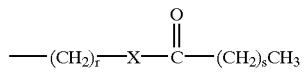

wherein r and s are each, independently of the other, integers representing a number of repeat —$CH_2$— groups, and $R_3$ is (i) an alkyl group, (ii) an aryl group, (iii) an arylalkyl group, or (iv) an alkylaryl. group, to form a diazopyridone compound of the formula

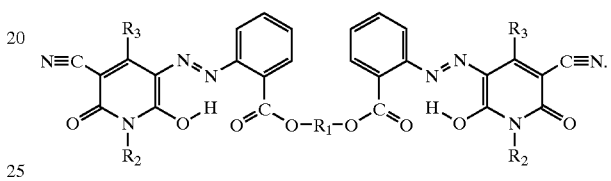

DETAILED DESCRIPTION OF THE INVENTION

Dianthranilate compounds are prepared according to the present invention by reacting isatoic anhydride with the selected diol in the presence of a base catalyst and a solvent and heating to form the desired product, as follows:

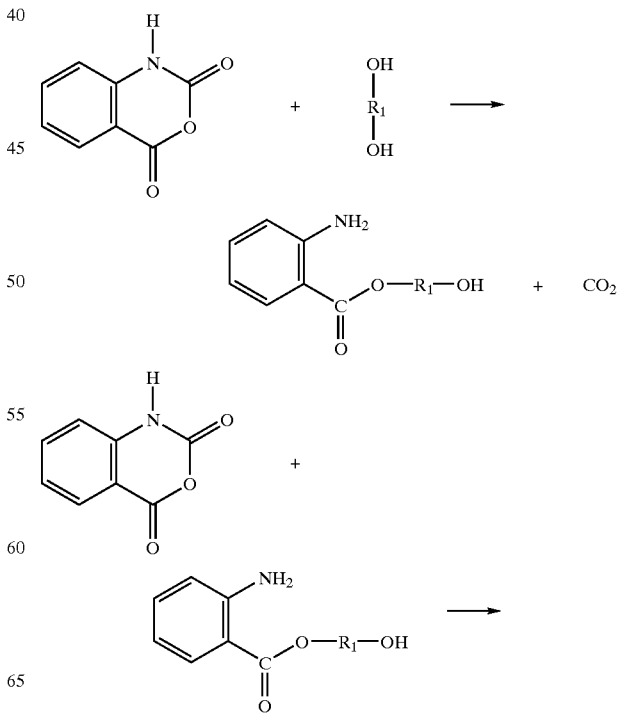

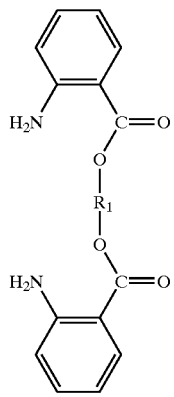

$+ \quad CO_2$

The selected diol is one wherein the hydroxy groups are either primary (i.e., connected to a carbon atom which is connected to one other carbon atom) or secondary (i.e., connected to a carbon atom which is connected to two other carbon atoms). In the diol of formula $R_1(OH)_2$, $R_1$ is an alkylene group (including linear, branched, saturated, unsaturated, and cyclic alkylene groups), in one embodiment with at least about 20 carbon atoms, in another embodiment with at least about 22 carbon atoms, in still another embodiment with at least about 24 carbon atoms, in another embodiment with at least about 26 carbon atoms, in yet another embodiment with at least about 28 carbon atoms, in still another embodiment with at least about 30 carbon atoms, in another embodiment with at least about 32 carbon atoms, in yet another embodiment with at least about 34 carbon atoms, and in still another embodiment with at least about 36 carbon atoms, and in one embodiment with no more than about 200 carbon atoms, in another embodiment with no more than about 100 carbon atoms, in yet another embodiment with no more than about 75 carbon atoms, in still another embodiment with no more than about 60 carbon atoms, in another embodiment with no more than about 50 carbon atoms, and in yet another embodiment with no more than about 40 carbon atoms, although the number of carbon atoms can be outside of these ranges. In a specific embodiment, $R_1$ is a branched alkyl group of the formula —$C_{36}H_{64+n}$— wherein n is an integer of 0, 1, 2, 3, 4, 5, 6, 7, 8, 9, or 10, which may include unsaturations and cyclic groups. One specific example of $R_1$ is a group of the formula

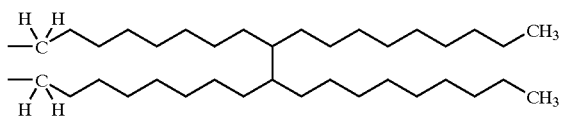

Examples of suitable $R_1(OH)_2$ compounds include a branched $C_{36}$ dimer diol commercially available from Uniqema (New Castle, Del.) under the trade name PRIPOL® 2033, including isomers of the formula

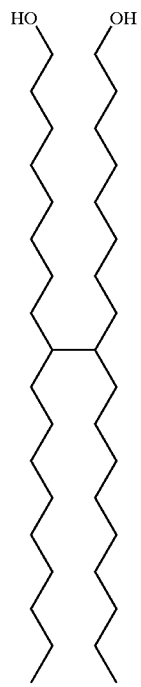

and other branched isomers (which may include unsaturations and cyclic groups) (further information on $C_{36}$ dimer diols of this type is disclosed in, for example, "Dimer Acids," *Kirk-Othmer Encyclopedia of Chemical Technology*, Vol. 8, 4$^{th}$ Ed. (1992), pp. 223 to 237, the disclosure of which is totally incorporated herein by reference) and the like.

Isatoic anhydride and the selected diol are present in any desired or effective relative amounts, in one embodiment at least about 2 moles of isatoic anhydride per every one mole of diol, in another embodiment at least about 2.05 moles of isatoic anhydride per every one mole of diol, in yet another embodiment at least about 2.1 moles of isatoic anhydride per every one mole of diol, and in still another embodiment at least about 2.2 moles of isatoic anhydride per every one mole of diol, and in one embodiment no more than about 5 moles of isatoic anhydride per every one mole of diol, in another embodiment no more than about 3 moles of isatoic anhydride per every one mole of diol, and in yet another embodiment no more than about 2.5 moles of isatoic anhydride per every one mole of diol, although the relative amounts of reactants can be outside of these ranges.

The catalyst is 1,4-diazabicyclo[2.2.2]octane, N,N,N', N'-tetramethylethylene diamine, or a mixture thereof. The catalyst is present in the reaction mixture in any desired or effective amount, in one embodiment at least about 0.2 mole of catalyst per every one mole of diol, in another embodiment at least about 0.22 mole of catalyst per every one mole of diol, in yet another embodiment at least about 0.25 mole of catalyst per every one mole of diol, and in still another embodiment at least about 0.5 mole of catalyst per every one mole of diol, and in one embodiment no more than about 2 moles of catalyst per every one mole of diol, in another embodiment no more than about 1 mole of catalyst per every one mole of diol, and in yet another embodiment no more than about 0.5 mole of catalyst per every one mole of diol, although the relative amount of catalyst can be outside of these ranges.

The reactants typically are present in a suitable solvent. The reactants can be either soluble or insoluble in the solvent, resulting in a homogeneous or a heterogeneous reaction mixture. Examples of suitable solvents include toluene, xylene, methyl ethyl ketone, ethyl acetate, butyl acetate, chlorobenzene, dioxane, dimethylformamide, N-methyl-2-pyrrolidinone, dimethylsulfoxide, sulfolane, pyridone, and the like, as well as mixtures thereof, with toluene and butyl acetate being preferred.

The reactants can be present in the solvent in any desired or effective relative amounts. The solvent is present in an amount of in one embodiment at least about 0.1 mole of diol per liter of solvent, in another embodiment at least about 0.25 mole of diol per liter of solvent, in yet another embodiment at least about 0.5 mole of diol per liter of solvent, and in still another embodiment at least about 0.75 mole of diol per liter of solvent, and is present in an amount of in one embodiment no more than about 3 moles of diol per liter of solvent, in another embodiment no more than about 2 moles of diol per liter of solvent, in yet another embodiment no more than about 1.5 moles of diol per liter of solvent, and in still another embodiment no more than about 0.75 mole of diol per liter of solvent, although the relative amount of solvent can be outside of these ranges.

The reaction mixture is heated to any desired or effective temperature, in one embodiment to a temperature of at least about 40° C., in another embodiment to a temperature of at least about 75° C., and in yet another embodiment to a temperature of at least about 100° C., and is heated in one embodiment to a temperature of no more than about 200° C. in another embodiment to a temperature of no more than about 170° C., and in yet another embodiment of no more than about 150° C., although the temperature can be outside of these ranges.

The reaction is carried out by heating for any desired or effective amount of time, in one embodiment for a period of at least about 1 hour, in another embodiment for a period of at least about 2.5 hours, and in yet another embodiment for a period of at least about 3 hours, and in one embodiment for a period of no more than about 10 hours, in another embodiment for a period of no more than about 6 hours, and in yet another embodiment for a period of no more than about 3.5 hours, although the reaction time can be outside of these ranges.

Subsequent to completion of the reaction, excess isatoic anhydride can be quenched, by, for example, the dropwise addition of a dilute solution (about 5 percent, for example) of aqueous sodium or potassium hydroxide to convert isatoic anhydride to the water-soluble sodium or potassium salt of anthranilic acid. Alternately, excess isatoic anhydride can be reacted with methanol or ethanol, which converts it to methyl or ethyl anthranilate, both of which are liquids soluble in common organic solvents, such as alcohols, ethers, ketones, esters, and the like.

The dianthranilate product can be separated from the reaction mixture by any desired or effective method. For example, liquid-liquid extraction, which may be desirable when the dianthranilate is not crystalline at ambient temperature, can be carried out between the organic phase and the aqueous phase of the mixture. (Said aqueous phase can be added when the reaction mixture is subjected to quenching with an aqueous solution; when such quenching is not carried out, water can be added to create the aqueous phase.) In the event of formation of an emulsion between these phases, which could make separation of the layers difficult or very slow, techniques known to those skilled in the art of extractive separation, such as, for example, adding more of the same or a different organic solvent to the organic layer, such as ethyl acetate or the like, and/or adding a salt, such as, for example, sodium chloride, potassium chloride, ammonium sulfate, or the like (typically in amounts from about 5 to about 30 percent by weight in water) can be performed. The organic phase can then, if desired, be dried by any desired or effective method, such as by drying over magnesium sulfate, or the like. The product can then be isolated by removal of the solvent by any desired or effective method, such as vacuum distillation or the like. If desired, the resulting product, while it is still dissolved in the organic phase, can be treated with acidic media, such as an acid-leached bentonite clay (available from Englehart Industries under the Trade name FILTROL® 24), which treatment can serve to remove any undesirable colored basic impurities.

The dianthranilate product can also be separated from the reaction mixture by precipitation using a non-solvent, which may be desirable when the dianthranilate product is crystalline. In this situation, a low alcohol, such as methanol or ethanol, is added to the reaction mixture in a molar amount greater than or equal to the amount of unreacted isatoic anhydride, either after cooling to room temperature or at a temperature of up to about 80° C., which serves to convert excess isatoic anhydride to the liquid methyl or ethyl anthranilate. Addition of a non-solvent for the dianthranilate, such as water, methanol, isopropanol, or the like is then used to precipitate the product, which can then be separated by filtration, washing with a suitable solvent, and drying.

The dianthranilate compounds prepared according to the present invention can be used as intermediates in the preparation of diazopyridone colorant molecules. The pyridones with which the dianthranilate compounds are reacted are of the general formula

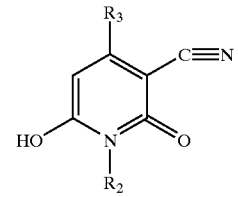

wherein $R_2$ is (i) an alkyl group (including linear, branched, saturated, unsaturated, cyclic, unsubstituted, and substituted alkyl groups, and wherein hetero atoms, such as oxygen, nitrogen, sulfur, silicon, phosphorus, and the like either may or may not be present in the alkyl group), in one embodiment with at least 1 carbon atom, in another embodiment with at least about 8 carbon atoms, in yet another embodiment with at least about 10 carbon atoms, in still another embodiment with at least about 12 carbon atoms, in another embodiment with at least about 14 carbon atoms, in yet another embodiment with at least about 16 carbon atoms, in still another embodiment with at least about 18 carbon atoms, in another embodiment with at least about 20 carbon atoms, in yet another embodiment with at least about 22 carbon atoms, in still another embodiment with at least about 24 carbon atoms, in another embodiment with at least about 26 carbon atoms, in yet another embodiment with at least about 28 carbon atoms, in still another embodiment with at least about 30 carbon atoms, in another embodiment with at least about 32 carbon atoms, in yet another embodiment with at least about 34 carbon atoms, and in still another embodiment with at least about 36 carbon atoms, and in one embodiment with no more than about 200 carbon atoms, in another embodiment with no more than about 100 carbon atoms, in yet another embodiment with no more than about 75 carbon atoms, in still another embodiment with no more than about 60 carbon atoms, in another embodiment with no more than about 50 carbon atoms, and in yet another embodiment with no more than about 40 carbon atoms, although the number of carbon atoms can be outside of these ranges, (ii) an aryl group (including unsubstituted and substituted aryl groups), in one embodiment with at least about 6 carbon atoms, in another embodiment with at least about 10 carbon atoms, in yet another embodiment with at least about 13 carbon atoms, in still another embodiment with at least about 14 carbon atoms, in another embodiment with at least about 16 carbon atoms, in yet another embodiment with at least about 17 carbon atoms, in still another embodiment with at least about 18 carbon atoms, in another embodiment with at least about 19 carbon atoms, in yet another embodiment with at least about 20 carbon atoms, in still another embodiment with at least about 21 carbon atoms, in another embodiment with at least about 22 carbon atoms, and in yet another embodiment with at least about 23 carbon atoms, and in one embodiment with no more than about 100 carbon atoms, in another embodiment with no more than about 75 carbon atoms, and in yet another embodiment with no more than about 50 carbon atoms, although the number of carbon atoms can be outside of these ranges, (iii) an arylalkyl group (including unsubstituted and substituted arylalkyl groups), in one embodiment with at least about 7 carbon atoms, in another embodiment with at least about 8 carbon atoms, in another embodiment with at least about 10 carbon atoms, in yet another embodiment with at least about 12 carbon atoms, in still another embodiment with at least about 14 carbon atoms, in another embodiment with at least about 16 carbon atoms, in yet another embodiment with at least about 18 carbon atoms, in still another embodiment with at least about 20 carbon atoms, in another embodiment with at least about 22 carbon atoms, in yet another embodiment with at least about 24 carbon atoms, in still another embodiment with at least about 26 carbon atoms, in another embodiment with at least about 28 carbon atoms, in yet another embodiment with at least about 30 carbon atoms, in still another embodiment with at least about 32 carbon atoms, in another embodiment with at least about 34 carbon atoms, in yet another embodiment with at least about 36 carbon atoms, in another embodiment with at least about 38 carbon atoms, in yet another embodiment with at least about 40 carbon atoms, and in still another embodiment with at least about 42 carbon atoms, and in one embodiment with no more than about 200 carbon atoms, in another embodiment with no more than about 100 carbon atoms, and in yet another embodiment with no more than about 44 carbon atoms, although the number of carbon atoms can be outside of these ranges, (iv) an alkylaryl group (including unsubstituted and substituted alkylaryl groups), in one embodiment with at least about 7 carbon atoms, in another embodiment with at least about 8 carbon atoms, in another embodiment with at least about 10 carbon atoms, in yet another embodiment with at least about 12 carbon atoms, in still another embodiment with at least about 14 carbon atoms, in another embodiment with at least about 16 carbon atoms, in yet another embodiment with at least about 18 carbon atoms, in still another embodiment with at least about 20 carbon atoms, in another embodiment with at least about 22 carbon atoms, in yet another embodiment with at least about 24 carbon atoms, in still another embodiment with at least about 26 carbon atoms, in another embodiment with at least about 28 carbon atoms, in yet another embodiment with at least about 30 carbon atoms, in still another embodiment with at least about 32 carbon atoms, in another embodiment with at least about 34 carbon atoms, in yet another embodiment with at least about 36 carbon atoms, in another embodiment with at least about 38 carbon atoms, in yet another embodiment with at least about 40 carbon atoms, and in still another embodiment with at least about 42 carbon atoms, and in one embodiment with no more than about 200 carbon atoms, in another embodiment with no more than about 100 carbon atoms, and in yet another embodiment with no more than about 44 carbon atoms, although the number of carbon atoms can be outside of these ranges, (v) an alkoxy group (including linear, branched, saturated, unsaturated, cyclic, unsubstituted, and substituted alkoxy groups, and wherein hetero atoms, such as oxygen, nitrogen, sulfur, silicon, phosphorus, and the like either may or may not be present in the alkyl portion of the alkoxy group), in one embodiment with at least 1 carbon atom, in another embodiment with at least about 8 carbon atoms, in yet another embodiment with at least about 10 carbon atoms, in still another embodiment with at least about 12 carbon atoms, in another embodiment with at least about 14 carbon atoms, in yet another embodiment with at least about 16 carbon atoms, in still another embodiment with at least about 18 carbon atoms, in another embodiment with at least about 20 carbon atoms, in yet another embodiment with at least about 22 carbon atoms, in still another embodiment with at least about 24 carbon atoms, in another embodiment with at least about 26 carbon atoms, in yet another embodiment with at least about 28 carbon atoms, in still another embodiment with at least about 30 carbon atoms, in another embodiment with at least about 32 carbon atoms, in yet another embodiment with at least about 34 carbon atoms, and in still another embodiment with at least about 36 carbon atoms, and in one embodiment with no more than about 200 carbon atoms, in another embodiment with no more than about 100 carbon atoms, in yet another embodiment with no more than about 75 carbon atoms, in still another embodiment with no more than about 60 carbon atoms, in another embodiment with no more than about 50 carbon atoms, and in yet another embodiment with no more than about 40 carbon atoms, although the number of carbon atoms can be outside of these ranges, (vi) an aryloxy group (including unsubstituted and substituted aryloxy groups), in one embodiment with at least about 6 carbon atoms, in another embodiment with at least about 10 carbon atoms, in yet another embodiment with at least about 13 carbon atoms, in still another embodiment with at least about 14 carbon atoms, in another embodiment with at least about 16 carbon atoms, in yet another embodiment with at least about 17 carbon atoms, in still another embodiment with at least about 18 carbon atoms, in another embodiment with at least about 19 carbon atoms, in yet another embodiment with at least about 20 carbon atoms, in still another embodiment with at least about 21 carbon atoms, in another embodiment with at least about 22 carbon atoms, and in yet another embodiment with at least about 23 carbon atoms, and in one embodiment with no more than about 100 carbon atoms, in another embodiment with no more than about 75 carbon atoms, and in yet another embodiment with no more than about 50 carbon atoms, although the number of carbon atoms can be outside of these ranges, (vii) an arylalkyloxy group (including unsubstituted and substituted arylalkyloxy groups), in one embodiment with at least about 7 carbon atoms, in another embodiment with at least about 8 carbon atoms, in another embodiment with at least about 10 carbon atoms, in yet another embodiment with at least about 12 carbon atoms, in still another embodiment with at least about 14 carbon atoms, in another embodiment with at least about 16 carbon atoms, in yet another embodiment with at least about 18 carbon atoms, in still another embodiment with at least about 20 carbon atoms, in another embodiment with at least about 22 carbon atoms, in yet another embodiment with at least about 24 carbon atoms, in still another embodiment with at least about 26 carbon atoms, in another embodiment with at least about 28 carbon atoms, in yet another embodiment with at least about 30 carbon atoms, in still another embodiment with at least about 32 carbon atoms, in another embodiment with at least about 34 carbon atoms, in yet another embodiment, with at least about 36 carbon atoms, in another embodiment with at least about 38 carbon atoms, in yet another embodiment with at least about 40 carbon atoms, and in still another embodiment with at least about 42 carbon atoms, and in one embodiment with no more than about 200 carbon atoms, in another embodiment with no more than about 100 carbon atoms, and in yet another embodiment with no more than about 44 carbon atoms, although the number of carbon atoms can be outside of these ranges, (viii) an alkylaryloxy group (including unsubstituted and substituted alkylaryloxy groups), in one embodiment with at least about 7 carbon atoms, in another embodiment with at least about 8 carbon atoms, in another embodiment with at least about 10 carbon atoms, in yet another embodiment with at least about 12 carbon atoms, in still another embodiment with at least about 14 carbon atoms, in another embodiment with at least about 16 carbon atoms, in yet another embodiment with at least about 18 carbon atoms, in still another embodiment with at least about 20 carbon atoms, in another embodiment with at least about 22 carbon atoms, in yet another embodiment with at least about 24 carbon atoms, in still another embodiment with at least about 26 carbon atoms, in another embodiment with at least about 28 carbon atoms, in yet another embodiment with at least about 30 carbon atoms, in still another embodiment with at least about 32 carbon atoms, in another embodiment with at least about 34 carbon atoms, in yet another embodiment with at least about 36 carbon atoms, in another embodiment with at least about 38 carbon atoms, in yet another embodiment with at least about 40 carbon atoms, and in still another embodiment with at least about 42 carbon atoms, and in one embodiment with no more than about 200 carbon atoms, in another embodiment with no more than about 100 carbon atoms, and in yet another embodiment with no more than about 44 carbon atoms, although the number of carbon atoms can be outside of these ranges, (ix) a polyalkyleneoxy group, wherein the alkyl portion of the repeat alkyleneoxy groups typically has from about 1 to about 12 carbon atoms, although the number of carbon atoms can be outside of these ranges, such as a polyethyleneoxy group, a polypropyleneoxy group, a polybutyleneoxy group, or the like, and wherein the number of repeat alkyleneoxy groups typically is from about 2 to about 50 repeat alkyleneoxy groups, although the number of repeat units can be outside of these ranges, (x) a polyaryleneoxy group, wherein the aryl portion of the repeat aryleneoxy groups typically has from about 6 to about 14 carbon atoms, although the number of carbon atoms can be outside of these ranges, such as a polyphenyleneoxy group, a polynaphthaleneoxy group, a polyphenanthreneoxy group, or the like, and wherein the number of repeat aryleneoxy groups typically is from about 2 to about 20 repeat aryleneoxy groups, although the number of repeat units can be outside of these ranges, (xi) a polyarylalkyleneoxy group, wherein the arylalkyl portion of the repeat arylalkyleneoxy groups typically has from about 7 to about 50 carbon atoms, although the number of carbon atoms can be outside of these ranges, such as a polybenzyleneoxy group, a polyphenylethyleneoxy group, or the like, and wherein the number of repeat arylalkyleneoxy groups typically is from about 2 to about 20 repeat arylalkyleneoxy groups, although the number of repeat units can be outside of these ranges, (xii) a polyalkylaryleneoxy group, wherein the alkylaryl portion of the repeat alkylaryleneoxy groups typically has from about 7 to about 50 carbon atoms, although the number of carbon atoms can be outside of these ranges, such as a polytolueneoxy group or the like, and wherein the number of repeat alkylaryleneoxy groups typically is from about 2 to about 20 repeat alkylaryleneoxy groups, although the number of repeat units can be outside of these ranges, (xiii) a heterocyclic group (including unsubstituted and substituted heterocyclic groups), typically with from about 2 to about 12 carbon atoms, and typically with from about 4 to about 18 ring atoms, although the number of carbon atoms and the number of ring atoms can be outside of these ranges, wherein the heteroatoms in the heterocyclic groups can be (but are not limited to) nitrogen, oxygen, sulfur, silicon, phosphorus, and the like, as well as mixtures thereof, (xiv) a silyl group (including unsubstituted and substituted silyl groups), (xv) a siloxane group (including unsubstituted and substituted siloxane groups), (xvi) a polysilylene group (including unsubstituted and substituted polysilylene groups), typically with from 2 to about 100 repeat silylene units, (xvii) a polysiloxane group (including unsubstituted and substituted polysiloxane groups), typically with from 2 to about 200 repeat siloxane units, although the number of repeat siloxane units can be outside of this range, or (xviii) a group of the formula

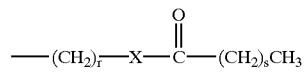

wherein r is an integer representing the number of repeat —CH$_2$— groups, in one embodiment being at least 1, in another embodiment at least about 5, and in yet another embodiment at least about 10, and in one embodiment being no more than about 100, in another embodiment no more than about 50, and in yet another embodiment no more than about 25, although the value of r can be outside of these ranges, and wherein s is an integer representing the number of repeating —CH$_2$— groups, in one embodiment being at least 1, in another embodiment at least about 5, and in yet another embodiment at least about 10, and in one embodiment being no more than about 100, in another embodiment no more than about 50, and in yet another embodiment no more than about 25, although the value of s can be outside of these ranges, wherein the substituents on the substituted alkyl, aryl, arylalkyl, alkylaryl, alkoxy, aryloxy, arylalkyloxy, alkylaryloxy, polyalkyleneoxy, polyaryleneoxy, polyarylalkyleneoxy, polyalkylaryleneoxy, heterocyclic, silyl, siloxy, polysilylene, and polysiloxy groups are hydroxy groups, halogen atoms, cyano groups, ether groups, aldehyde groups, ketone groups, carboxylic acid groups, ester groups, amide groups, carbonyl groups, thiocarbonyl groups, sulfate groups, sulfonate groups, sulfide groups, sulfoxide groups, phosphate groups, nitrile groups, mercapto groups, nitro groups, nitroso groups, sulfone groups, acyl groups, acid anhydride groups, azide groups, cyanato groups, isocyanato groups, thiocyanato groups, isothiocyanato groups, mixtures thereof, and the like, wherein the substituents on the silylene, siloxy, polysilylene, and polysiloxy groups can also be alkyl groups, aryl groups, arylalkyl groups, and alkylaryl groups, wherein two or more substituents can be joined together to form a ring.

Some specific examples of suitable R$_2$ groups include (but are not limited to) ethyl, of the formula —CH$_2$CH$_3$, n-butyl, of the formula —(CH$_2$)$_3$CH$_3$, n-octyl, of the formula —(CH$_2$)$_7$CH$_3$, n-decyl, of the formula —(CH$_2$)$_9$CH$_3$, n-dodecyl, of the formula —(CH$_2$)$_{11}$CH$_3$, n-tetradecyl, of the formula —(CH$_2$)$_{13}$CH$_3$, cetyl, of the formula —(CH$_2$)$_{15}$CH$_3$, stearyl, of the formula —(CH$_2$)$_{17}$CH$_3$, 2-ethylhexyl, of the formula

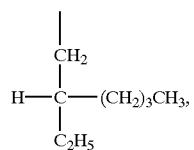

abietyl, including groups of the formula

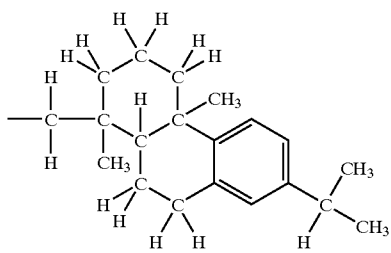

as well as hydrogenated and dehydrogenated isomers of the above formula that are also derivatives of the rosin-derived natural product abietic acid, such as didehydroabietyl and the like, 3-propyl octadecanoyl, of the formula

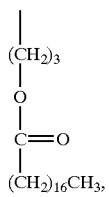

2,2-dimethyl-1,3-dioxolane-4-methylene, of the formula

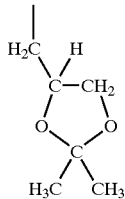

and the like.

$R_3$ is (i) an alkyl group (including linear, branched, saturated, unsaturated, cyclic, unsubstituted, and substituted alkyl groups, and wherein hetero atoms, such as oxygen, nitrogen, sulfur, silicon, phosphorus, and the like can be present in the alkyl group), typically with from 1 to about 100 carbon atoms, preferably with from about 1 to about 10 carbon atoms, and more preferably with from about 1 to about 5 carbon atoms, although the number of carbon atoms can be outside of these ranges, (ii) an aryl group (including unsubstituted and substituted aryl groups), typically with from about 6 to about 100 carbon atoms, and preferably with from about 6 to about 10 carbon atoms, although the number of carbon atoms can be outside of these ranges, (iii) an arylalkyl group (including unsubstituted and substituted arylalkyl groups), typically with from about 7 to about 100 carbon atoms, and preferably with from about 7 to about 10 carbon atoms, although the number of carbon atoms can be outside of these ranges, or (iv) an alkylaryl group (including unsubstituted and substituted alkylaryl groups), typically with from about 7 to about 100 carbon atoms, and preferably with from about 7 to about 10 carbon atoms, although the number of carbon atoms can be outside of these ranges, wherein the substituents on the substituted alkyl, aryl, arylalkyl, and alkylaryl groups can be (but are not limited to) hydroxy groups, halogen atoms, amine groups, imine groups, ammonium groups, pyridine groups, pyridinium groups, ether groups, aldehyde groups, ester groups, amide groups, carbonyl groups, thiocarbonyl groups, sulfate groups, sulfonate groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, cyanato groups, isocyanato groups, thiocyanato groups, isothiocyanato groups, mixtures thereof, and the like, wherein two or more substituents can be joined together to form a ring.

Specific examples of suitable $R_3$ groups include methyl (—$CH_3$), linear alkyl groups of the formula —$(CH_2)_cCH_3$ wherein c is an integer of 1, 2, 3, 4, 5, 6, 7, 8, or 9, and the like.

For example, diazopyridone colorant molecules can be prepared by diazotization of the correspondingly substituted dimeric aniline with nitrosylsulfuric acid under cold temperature conditions, followed by coupling with the correspondingly substituted pyridone in a buffered alkaline aqueous solution under cold temperature conditions, as follows:

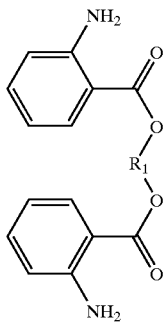 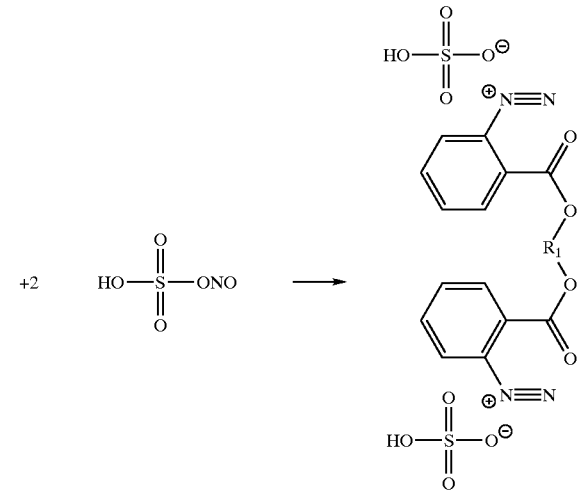

-continued

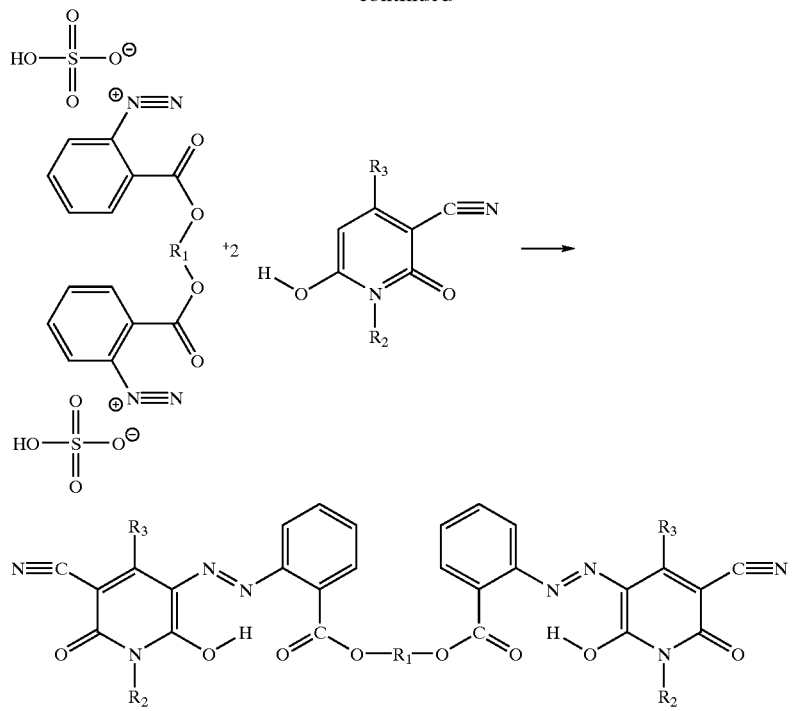

More specifically, the correspondingly substituted dianiline is first subjected to a diazotization reaction by dissolving it in acetic acid diluted with a solvent and, optionally, a second acid, such as sulfuric acid, dodecylbenzene sulfonic acid, propionic acid, hydrochloric acid, phosphoric acid, any other acid useful for a diazotization reaction, or the like, as well as mixtures thereof. The solvent can be any solvent useful in a diazotization reaction, such as water, acetone, dimethylformamide, dimethyacetamide, tetrahydrofuran, dimethoxyethane, analogous higher-boiling ether solvents, and the like, as well as mixtures thereof.

The solvent and the dianiline are present in any desired or effective relative amounts; if, for purposes of determining relative amounts, "solvent" is defined to include whatever solvent has been selected plus any amount of acetic acid and second acid present, the reactants are present in this combined solvent in relative amounts of in one embodiment at least about 100 grams of substituted dianiline per liter of solvent, in another embodiment at least about 200 grams of substituted dianiline per liter of solvent, and in yet another embodiment at least about 230 grams of substituted dianiline per liter of solvent, and in one embodiment of no more than about 400 grams of substituted dianiline per liter of solvent, in another embodiment of no more than about 300 grams of substituted dianiline per liter of solvent, and in yet another embodiment of no more than about 270 grams of substituted dianiline per liter of solvent, although the relative amounts can be outside of these ranges.

The acetic acid is present in any desired or effective amount, in one embodiment at least about 1 gram of acetic acid per gram of substituted dianiline, in another embodiment at least about 2 grams of acetic acid per gram of substituted dianiline, and in yet another embodiment at least about 3 grams of acetic acid per gram of substituted dianiline, and in one embodiment no more than about 10 grams of acetic acid per gram of substituted dianiline, in another embodiment no more than about 7 grams of acetic acid per gram of substituted dianiline, and in yet another embodiment no more than about 5 grams of acetic acid per gram of substituted dianiline, although the relative amounts can be outside of these ranges.

When present, the optional second acid is present in any desired or effective amount, in one embodiment at least about 0.05 gram of acid per gram of substituted dianiline, and in another embodiment at least about 0.1 gram of acid per gram of substituted dianiline, and in one embodiment no more than about 0.5 grams of acid per gram of substituted dianiline, in another embodiment no more than about 0.3 grams of acid per gram of substituted dianiline, and in yet another embodiment no more than about 0.2 grams of acid per gram of substituted dianiline, although the relative amounts can be outside of these ranges.

In the mixture comprising the selected solvent, any optional second acid, and acetic acid, the acetic acid is present in any desired or effective amount, in one embodiment at least about 50 percent by volume of the mixture, in another embodiment at least about 70 percent by volume of the mixture, in yet another embodiment at least about 75 percent by volume of the mixture, and in still another embodiment at least about 95 percent by volume of the mixture, although the relative amount can be outside of these ranges.

Upon complete dissolution of the ingredients, the mixture is cooled, in one embodiment to a temperature of no more than about +15° C., in another embodiment to a temperature of no more than about +10° C., in yet another embodiment to a temperature of no more than about +5° C., in still another embodiment to a temperature of no more than about +3° C., and in one embodiment to a temperature of no lower than about −5° C., and in another embodiment to a temperature of no lower than about −10° C., although the temperature can be outside of these ranges.

Thereafter, nitrosylsulfuric acid is added to the mixture in any desired or effective amount, in one embodiment at least about 2 moles of nitrosylsulfuric acid per mole of substituted dianiline (i.e., at least about 1 mole of nitrosylsulfuric acid per mole of aniline moiety in the dianiline), and in another embodiment at least about 2.1 moles of nitrosylsulfuric acid per mole of substituted dianiline, and in one embodiment no more than about 3 moles of nitrosylsulfuric acid per mole of substituted dianiline, in another embodiment no more than about 2.5 moles of nitrosylsulfuric acid per mole of substituted dianiline, and in yet another embodiment no more than about 2.25 moles of nitrosylsulfuric acid per mole of substituted dianiline, although the relative amounts can be outside of these ranges. In a specific embodiment, the nitrosylsulfuric acid is added dropwise at a rate such that the temperature of the reaction mixture does not exceed 15° C.

The reaction to form the diazonium salt is essentially instantaneous, and upon completion of addition of the nitrosylsulfuric acid the reaction is essentially complete, although, if desired, a qualitative test can be performed to confirm reaction completion.

Thereafter, residual excess nitrosylsulfuric acid present in the reaction mixture can be quenched by the addition of a quenching agent, such as sulfamic acid, urea, or the like as well as mixtures thereof, in any desired or effective amount, in one embodiment at least about 0.01 mole of quenching agent per mole of nitrosylsulfuric acid (i.e., per mole of nitrosylsulfuric acid originally added to the reaction mixture), in another embodiment at least about 0.05 mole of quenching agent per mole of nitrosylsulfuric acid, and in yet another embodiment at least about 0.1 mole of quenching agent per mole of nitrosylsulturic acid, and in one embodiment no more than about 0.5 mole of quenching agent per mole of nitrosylsulfuric acid, in another embodiment no more than about 0.3 mole of quenching agent per mole of nitrosylsulfuric acid, and in yet another embodiment no more than about 0.2 mole of quenching agent per mole of nitrosylsulfuric acid, although the amount can be outside of these ranges. Upon completion of the reaction, the reaction mixture contains the corresponding diazonium salt.

A precursor solution of the pyridone having the desired substituents thereon is prepared in an appropriate solvent, such as a mixture of water, organic solvents, including lower alcohols such as methanol, ethanol, isopropanol, and the like, water-miscible nonbasic organic solvents such as tetrahydrofuran, acetone, dimethoxyethane, N,N-dimethylformamide, N,N-dimethylacetamide, and the like, as well as mixtures thereof. Mixtures of water with an organic solvent can be helpful for ease of solvating inorganic or organic salts that are a reaction by-product. In this instance, water and the organic solvent are present in any desired or effective relative amounts, in one embodiment at least about 0.25 gram of organic solvent per gram of water, in another embodiment at least about 0.3 gram of organic solvent per gram of water, and in yet another embodiment at least about 0.4 gram of organic solvent per gram of water, and in one embodiment no more than about 4 grams of organic solvent per gram of water, in another embodiment no more than about 3 grams of organic solvent per gram of water, and in yet another embodiment no more than about 2 grams of organic solvent per gram of water, although the relative amounts can be outside of these ranges.

The pyridone is present in the precursor solution in any desired or effective amount, in one embodiment at least about 10 grams of pyridone per liter of solvent, in another embodiment at least about 30 grams of pyridone per liter of solvent, and in yet another embodiment at least about 50 grams of pyridone per liter of solvent, and in one embodiment no more than about 200 grams of pyridone per liter of solvent, in another embodiment no more than about 100 grams of pyridone per liter of solvent, and in yet another embodiment no more than about 70 grams of pyridone per liter of solvent, although the relative amounts can be outside of these ranges.

The pyridone precursor solution is maintained at an alkaline pH, typically of at least about 10, and in one embodiment no more than about 14, and in another embodiment no more than about 12, although the pH can be outside of these ranges. The pyridone precursor solution can contain a mixture of a base and an optional buffering salt.

Examples of suitable bases include mineral bases, such as sodium hydroxide, potassium hydroxide, and the like, as well as water-miscible organic tertiary amines, such as triethanolamine, N,N-diethylethanolamine, and the like, as well as mixtures thereof, present in any desired or effective amount, in one embodiment at least about 1 mole of base per mole of pyridone, in another embodiment at least about 2 moles of base per mole of pyridone, in yet another embodiment at least about 3 moles of base per mole of pyridone, and in still another embodiment at least about 5 moles of base per mole of pyridone, and in one embodiment no more than about 10 moles of base per mole of pyridone, in another embodiment no more than about 7 moles of base per mole of pyridone, and in yet another embodiment no more than about 5 moles of base per mole of pyridone, although the relative amounts can be outside of these ranges.

Examples of suitable optional buffer salts include those corresponding to the principal acid solvent; for example, when the principal acid solvent is acetic acid, suitable buffers include sodium acetate, potassium acetate, sodium hydrogenphosphate, citric acid, and the like, as well as mixtures thereof. When present, the optional buffer salt is present in any desired or effective amount, in one embodiment at least about 1 mole of buffer per mole of pyridone, in another embodiment at least about 2 moles of buffer per mole of pyridone, in yet another embodiment at least about 3 moles of buffer per mole of pyridone, and in still another embodiment at least about 5 moles of buffer per mole of pyridone, and in one embodiment no more than about 10 moles of buffer per mole of pyridone, in another embodiment no more than about 7 moles of buffer per mole of pyridone, and in yet another embodiment no more than about 5 moles of buffer per mole of pyridone, although the relative amounts can be outside of these ranges. In a specific embodiment, upon dissolution of the pyridone, the thus-formed precursor pyridone solution can be filtered to remove any undissolved solids.

The solution containing the diazonium salt, maintained at a cold temperature, is then slowly added to the pyridone solution in any desired or effective relative amounts, in one embodiment at least about 2 moles of pyridone per mole of diazonium salt, in another embodiment at least about 2.1 moles of pyridone per mole of diazonium salt, and in yet another embodiment at least about 2.25 moles of pyridone per mole of diazonium salt, and in one embodiment no more than about 4 moles of pyridone per mole of diazonium salt, in another embodiment no more than about 3 moles of pyridone per mole of diazonium salt, and in yet another embodiment no more than about 2.5 moles of pyridone per mole of diazonium salt, although the relative amounts can be outside of these ranges, resulting in the immediate formation of a bright yellow precipitate. Thereafter, the yellow precipitate can be collected by filtration and, if desired, washed.

Precursor pyridones can be prepared by any desired or effective method, such as that disclosed in, for example, "Investigation of the Reaction Conditions for the Synthesis of 4,6-Disubstituted-3-cyano-2-pyridones and 4-Methyl-3-cyano-6-hydroxy-2-pyridone," D. Z. Mijin et al., *J. Serb. Chem. Soc.*, Vol. 59, No. 12, p. 959 (1994); "Synthesis of Isoquinoline Alkaloids. II. The Synthesis and Reactions of 4-Methyl-3-pyridinecarboxaldehyde and Other 4-Methyl-3-substituted Pyridines, J. M. Bobbitt et al., *J. Org. Chem.*, Vol 25, p. 560 (1960); "Synthesis and Dyeing Characteristics of 5-(4-Arylazophenyl)azo-3-cyano-4-methyl-6-hydroxy-2-pyridones," J. M. Kanhere et al., *Indian Journal of Textile Research*, Vol. 13, p. 213 (1988): "Synthesis of Some Pyridone Azo Dyes from 1-Substituted 2-Hydroxy-6-pyridone Derivatives and their Colour Assessment," C. Chen et al., *Dyes and Pigments*, Vol. 15, p. 69 (1991); "Synthesis of 3 Cyano-6-hydroxy-5-(2-(perfluoroalkyl)phenylazo)-2-pyridones and their Application for Dye Diffusion Thermal Transfer Printing," M. Matsui et al., *Bull. Chem. Soc. Jpn.*, 1993, Vol. 66, Iss. 6, Pp. 1790–4; "Synthesis of N-alkylcyanopyridones," B. Peng et al., *Faming Zhuanli Shenqing Gongkai Shuomingshu* (1997), CN 1158845; "Synthesis of 1-Butyl-3-cyano-4-methyl-6-hydroxypyrid-2-one," X. Kong et al., *Huaxue Shiji* (1998), 20(1), 58–59; "Regioselective Conversion of 3 Cyano-6-hydroxy-2-pyridones into 3 Cyano-6-amino-2-pyridones," A. R. Katritzky et al., *J. Heterocycd. Chem.* (1995), 32(3), 1007–10; "The Synthesis of Some Hetarylazopyridone Dyes and Solvent Effects on their Absorption Spectra," N. Ertan et al., *Dyes Pigm.* (1995), 27(4), 313–20; "Process for the Preparation of Pyridone Compounds," H. Schmid, Ger. Offen. DE 4314430 (1994); "Tautomerism of 4-Methyl-6-hydroxy-2-pyridone derivatives," H. Liu et al., *Dalian Ligong Daxue Xuebao* (1992), 32(4), 405–11; "Preparation of 1-Alkyl-3-cyano-4-methyl-6-hydroxy-2-pyridone-type Mixed Azo Coupling Components," J. Prikryl et al., *Czech.* (1991) 8 pp. CODEN: CZXXA9 CS 273045 B1 19911220 CAN 118:256604 AN 1993:256604 CAPLUS; "Structural Characteristics of Hydroxypyridone Derivatives," Q. Peng et al., *Dalian Ligong Daxue Xuebao* (1991), 31(3), 279–86; and "6-Hydroxypyridin-2-ones," F. Schmidt, Ger. Offen. DE 2845863 (1980); the disclosures of each of which are totally incorporated herein by reference.

Specific embodiments of the invention will now be described in detail. These examples are intended to be illustrative, and the invention is not limited to the materials, conditions, or process parameters set forth in these embodiments. All parts and percentages are by weight unless otherwise indicated.

EXAMPLE I

A dianthranilate compound of the formula

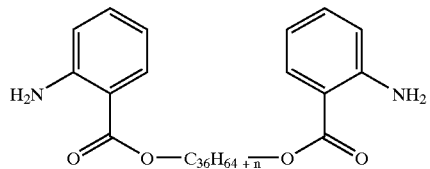

wherein $C_{36}H_{64+n}$ was a branched alkylene group which may include unsaturations and cyclic groups, wherein n is an integer of 0, 1, 2, 3, 4, 5, 6, 7, 8, 9, or 10, and wherein one isomer thereof was of the formula

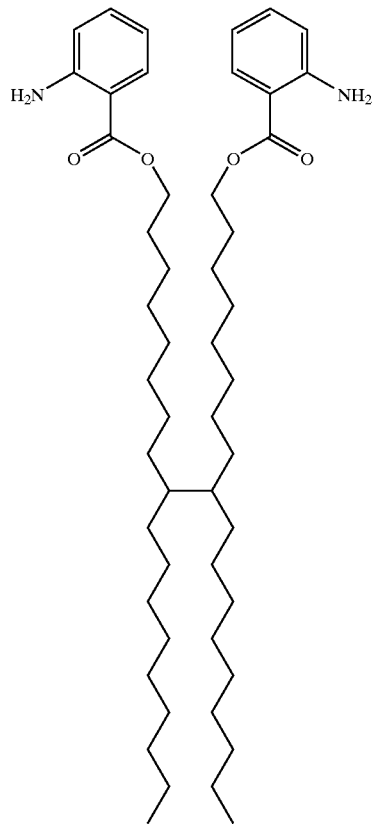

was prepared as follows. Into a 3 liter resin kettle equipped with a mechanical stirrer (glass shaft, TEFLON® blade), water condenser, and thermometer was sequentially charged: isatoic anhydride (203.9 grams, 1.25 mol; obtained from Sigma-Aldrich, Milwaukee, Wis.), PRIPOL® 2033 (C-36 dimer diol including isomers of the formula

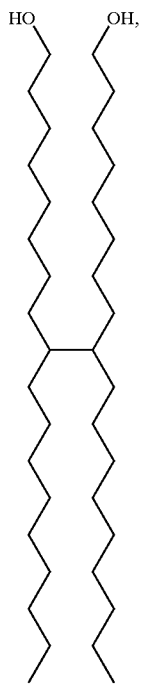

267 grams, 0.5 mol, obtained from Uniqema, New Castle, Del.), 1,4-diazabicyclo[2.2.2]octane (28 grams, 0.25 mol; obtained from Sigma-Aldrich), and toluene (750 milliliters). The heterogeneous mixture thus formed was heated to 115° C. (internal temperature). During the ensuing reaction, evolution of gaseous $CO_2$ byproduct was observed as frothing close to the stirrer shaft. After 3.5 hours of heating time, the bubbling subsided and $^1$H-NMR sample analysis indicated that the reaction was complete. The reaction was cooled to room temperature, and a 1.0 Molar aqueous solution of sodium hydroxide (500 milliliters, 0.5 mol) was added to the mixture. An emulsion resulted, along with some evolution of $CO_2$ gas (from quenching of excess isatoic anhydride), and the mixture was divided into two 2 liter separatory funnels. Into each funnel was added ethyl acetate (350 milliliters) to break up the emulsion in the organic phase, followed by the addition of a concentrated aqueous sodium chloride (brine) solution whereby the volume ratio of organic phase to aqueous phase was about 2 to 1. The organic phase was washed with 5×300 milliliter aliquots of brine solution until the pH was neutral. The tea-brown organic layer extracts obtained were combined, dried over anhydrous $MgSO_4$ powder, and then filtered. The solvents were removed by distillation in vacuo with a rotary evaporator, giving a honey-brown viscous oil which was subsequently dried under high vacuum to give 372 grams (96 percent yield) of product. The purity of the dianthranilate product was observed to be very high by $^1$H-NMR spectroscopy, estimated at 97 percent, with 3 percent attributed to residual toluene solvent. $^1$H-NMR spectral assignments (300 MHz, $CDCl_3$): 7.85 ppm (doublet, 2H integration), 7.22 ppm (triplet, 2H), 6.60 ppm (superimposed doublet+triplet, 4H), 5.7 ppm (broad singlet), 4.25 ppm (triplet, $CH_2OC=O$, 4H), 1.75 ppm to 0.8 ppm (aliphatic CH, $CH_2$, $CH_3$ protons, 3 signals totaling 80 H integration).

EXAMPLE II

Into a 5 liter round-bottom flask were charged the following materials in sequential order: isatoic anhydride (448.6 grams, 2.75 mol, obtained from Sigma-Aldrich), PRIPOL® 2033 (667.5 grams, 1.25 mol, obtained from Uniqema), 1,4-diazabicyclo[2.2.2]octane (35 grams, 0.313 mol; obtained from Sigma-Aldrich), and toluene (1,250 grams; density 0.865; 1,445 milliliters). The vessel was filled to approximately 60 percent volume capacity. The resulting mixture was heated in a heating mantle to reach an internal reaction temperature of 115° C. The mixture was heated under toluene reflux for 3 hours, and then cooled to 50° C. The mixture was then transferred to a separatory funnel, into which was also added 400 grams of 5 percent aqueous sodium hydroxide and 400 grams of ethyl acetate. These ingredients were then mixed together by turning the funnel upside down 5 times, venting any accumulated gases between each rotation. This mixture was then allowed to separate. Thereafter, the lower aqueous layer was drained and 5×150 gram washes using 5 percent aqueous sodium hydroxide were performed, draining the aqueous extract each time until no more brown color was noticeable. Aqueous washes with 10 percent aqueous sodium chloride followed afterward, about 3×400 gram portions, until the pH was neutral. The organic phase was then isolated, mixed with 100 grams of anhydrous $MgSO_4$ powder to absorb residual water, and subsequently filtered. The solution was then transferred into a 5 liter distillation flask to remove the toluene and ethyl acetate solvents under high vacuum at a temperature of about 100° C. The dianthranilate product was obtained as a viscous dark brown oil in 89 percent yield (867.5 grams). $^1$H-NMR spectral analysis of this material was in agreement with results from Example I.

EXAMPLE III

A solution of PRIPOL® 2033 dimer diol (181.8 grams, 0.339 mol), isatoic anhydride (167 grams, 1.00 mol), and 1,4-diazabicyclo[2.2.2]octane (22.4 grams, 0.20 mol) in 600 milliliters of dimethylformamide in a 4 liter beaker was stirred and heated to 105° C. Vigorous gas evolution occurred. After 15 minutes the temperature was raised to 155° C. After 1 hour the reaction mixture was cooled to about 50° C., then was treated with methanol (1,900 milliliters), followed by addition of water (100 milliliters). A two-phase system resulted. The layers were separated and the viscous, brown, bottom layer was washed with 2×500 milliliter portions of methanol by vigorously stirring followed by separating by decantation. The product was dried on a rotary evaporator for 0.5 hour (bath temperature of 85° C.) to give the dianthranilate as a viscous, light brown oil, 222 grams (84 percent) which was shown by $^1$H-NMR spectroscopy to be about 95 percent pure.

EXAMPLE IV

A colorant of the formula

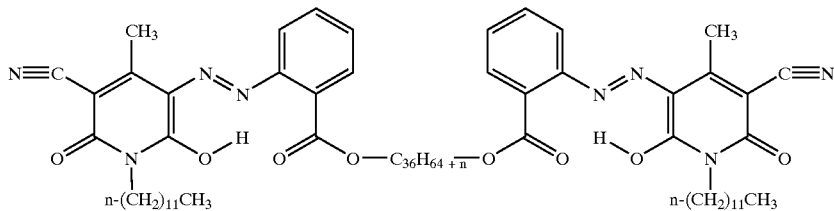

wherein $C_{36}H_{64+n}$ was a branched alkylene group which may include unsaturations and cyclic groups, wherein n is an integer of 0, 1, 2, 3, 4, 5, 6, 7, 8, 9, or 10, and wherein one isomer thereof was of the formula wherein $C_{36}H_{64+n}$ was a branched alkylene group which may include unsaturations and cyclic groups, wherein n is an integer of 0, 1, 2, 3, 4, 5, 6, 7, 8, 9, or 10, and wherein one isomer thereof was of the formula

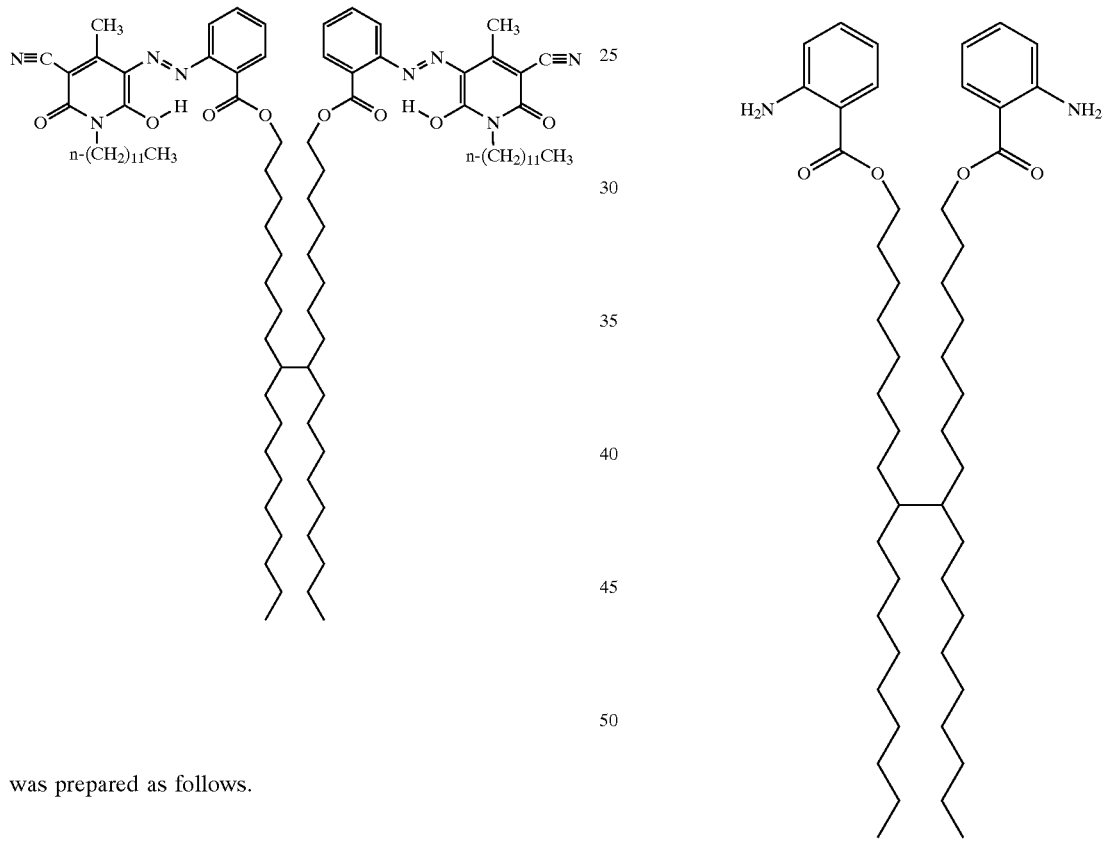

was prepared as follows.

A dimer ester anthranilate of the formula

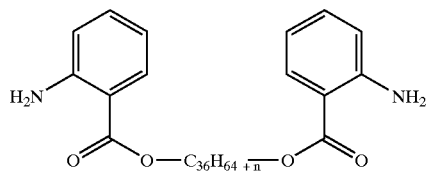

was prepared as follows. Into a 3 liter kettle equipped with a mechanical stirrer, water condenser, and thermometer was sequentially charged: isatoic anhydride (203.9 grams, 1.25 mol; obtained from Sigma-Aldrich, Milwaukee, Wis.), PRI-POL® 2033 (C-36 dimer diol mixture including isomers of the formula

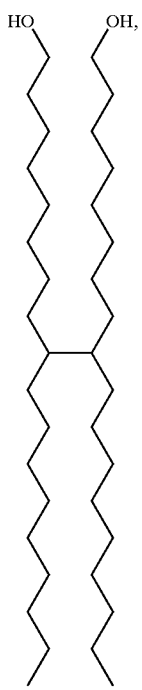

as well as other branched isomers which may include unsaturations and cyclic groups; 267 grams, 0.5 mol, obtained from Uniqema, New Castle, Del.; further information on $C_{36}$ dimer diols of this type is disclosed in, for example, "Dimer Acids," *Kirk-Othmer Encyclopedia of Chemical Technology*, Vol. 8, 4$^{th}$ Ed. (1992), pp. 223 to 237, the disclosure of which is totally incorporated herein by reference), 1,4-diazabicyclo[2.2.2]octane (28 grams, 0.25 mol; obtained from Sigma-Aldrich Co.), and toluene (750 milliliters). The heterogeneous mixture thus formed was heated to 115° C. (internal temperature). During the ensuing reaction, evolution of gaseous $CO_2$ byproduct was observed. After approximately 3 hours of heating time, the reaction was complete. The mixture was cooled to room temperature and a 1.0 Molar aqueous solution of sodium hydroxide (500 milliliters, 0.5 mol) was added to the mixture. An emulsion resulted, along with some evolution of $CO_2$ gas (from quenching of excess isatoic anhydride), and the mixture was divided into two 2 liter separatory funnels. Into each funnel was added ethyl acetate (350 milliliters) to break up the emulsion in the organic phase, followed by the addition of brine (saturated aqueous sodium chloride) solution whereby the volume ratio of organic phase to aqueous phase was about 2 to 1. The organic phase was washed with 5×300 milliliter aliquots of brine solution until the pH was neutral. The tea-brown organic layer extracts obtained were combined, dried over anhydrous $MgSO_4$ powder, and then filtered. The solvents were removed by distillation in vacuo with a rotary evaporator, giving an amber viscous oil which was subsequently dried under high vacuum to give 372 grams (96 percent yield) of product. The purity of the dimer ester anthranilate product was observed to be very high by $^1$H-NMR spectroscopy, estimated at 97 percent, with 3 percent attributed to residual toluene solvent. $^1$H-NMR spectral assignments (300 MHz, $CDCl_3$): 7.85 ppm (doublet, 2H integration), 7.22 ppm (triplet, 2H), 6.60 ppm (superimposed doublet+triplet, 4H), 5.7 ppm (broad singlet), 4.25 ppm (triplet, $CH_2OC=O$, 4H), 1.75 ppm to 0.8 ppm (aliphatic CH, $CH_2$, $CH_3$ protons, 3 signals totaling 80 H integration).

Into a 2 liter round-bottom flask equipped with mechanical stirrer and Dean Stark trap was charged melted dodecylamine (185.0 grams, 1.0 mol; melting point 30 to 32° C.; obtained from Akzo Nobel Chemicals, Mississauga, Ontario), followed with ethyl cyanoacetate (135.6 grams, 1.2 mol, density 1.06 grams per milliliter; obtained from Spectrum Chemicals, New Brunswick, N.J.). The colorless mixture was stirred and heated to 120° C. for a period of 1 hour, during which time a liquid by-product formed and was distilled away. To the hot reaction mixture stirring at 120° C. internal temperature was then sequentially added the solvent N,N-dimethylformamide (320 grams, obtained from Caledon Labs, Brampton, Ontario), ethyl acetoacetate (260.0 grams, 2.0 mol, density 1.02 grams per milliliter; obtained from Lonza Group, Germany), and piperazine (192.2 grams, 2.0 mol; obtained from Spectrum Chemicals, New Brunswick, N.J.). The resultant mixture was heated to 110° C. internal temperature for a period of 4 hours, during which time more by-product was distilled away. After this time, a golden brown viscous solution formed and was then allowed to cool to room temperature. The solution was carefully poured, with vigorous stirring and at room temperature, into a prepared solution of methanol (1,624 grams), deionized water (684 grams), and concentrated nitric acid (322 grams, 3.6 mol). A beige solid material precipitated immediately, and the resulting slurry was stirred for 30 minutes. The slurry was vacuum filtered, and the solid filter cake was rinsed several times with 500 milliliter portions of a solvent mixture comprising 70 percent by volume methanol and 30 percent by volume water, until the conductivity of the filtrate was less than 200 microSiemens per centimeter. The solid cake was dried at 40° C. under vacuum for 24 hours to give 277 grams (87 percent yield) of the dodecyl pyridone product as a light beige solid. $^1$H-NMR spectral analysis indicated that the product was of high purity, with no evidence of contaminants exceeding approximately 2 percent of the product yield. $^1$H-NMR spectral assignments (300 MHz, DMSO-$d_6$): 5.6 ppm (singlet, H at ring position C-5), 3.88 ppm (broad triplet, 2H, $CH_2$ adjacent ring N), 2.2 ppm (singlet, 3H, $CH_3$ at ring position C-4), 1.6 ppm to 0.8 ppm ($CH_2$ and $CH_3$ protons from dodecyl group, 3 signals totaling 65 H integration).

Into a 1 liter three neck round bottom flask equipped with a TEFLON® coated mechanical stirrer, 125 milliliter pressure-equalized dropping funnel, and cold-temperature thermometer was charged the dimer ester anthranilate prepared above (108 grams, 0.139 mol), followed sequentially with 210 milliliters of glacial acetic acid, 18 milliliters of concentrated sulfuric acid, 20 milliliters of deionized water, and 20 milliliters of propionic acid (obtained from Sigma-Aldrich Co.). The dark brown solution was chilled to an internal temperature of +3° to +5° C. Nitrosylsulfuric acid (NSA, commercial solution containing 40 percent by weight NSA in sulfuric acid, obtained from Sigma-Aldrich Co.; 56 milliliters, 0.285 mol) was then charged into the dropping funnel and was dripped slowly into the dianthranilate solution so as to keep the internal temperature between +3° and +5° C. and to minimize any frothing from emission of $NO_X$ gases. After about 1.5 hours, the NSA addition was completed, and a phosphomolybdic acid test of the diazonium salt solution indicated that the diazotization reaction was also complete. A small portion of sulfamic acid (1 gram, 0.01 mol) was then added to the mixture to quench any residual NSA, and the mixture was stirred for an additional 15 minutes.

The coupler solution of dodecyl pyridone was prepared using a 10 liter graduated beaker equipped with a mechanical stirrer. Into this vessel was charged sodium hydroxide (55 grams, 1.39 mol) and sodium acetate (114 grams, 1.39 mol), followed with deionized water (3.5 liters) and isopropanol (2.5 liters). Once all of the ingredients had dissolved, the dodecylpyridone prepared above was added to the solution and stirred vigorously until all solids were dissolved. The cold diazonium salt solution was then slowly poured into the dodecylpyridone coupling solution at room temperature. An instant bright yellow precipitate was formed, and after complete addition, the resulting slurry was stirred for an additional 0.5 to 1 hour prior to recovering the colorant material. The yellow slurry was vacuum filtered through a 3 micron hydrophobic membrane. The yellow filter cake was then reslurried again into a 20:80 mixture of isopropanol:deionized water, stirred for 30 minutes, and then filtered again. The filter cake was then subjected to the following treatment several times: redispersion into 1 liter of deionized water, stirring for 30 minutes, then filtration through a 3 micron hydrophobic membrane, until the pH of the resulting filtrate was greater than 5.0 and the conductivity of the filtrate was below 10 microSiemens per centimeter. The cake was then dried in a vacuum-oven at 30° C. over 36 hours, affording 192.6 grams (96.3 percent yield) of the crude product as a mustard-yellow granular powder, melting point range of 123 to 134 ° C. The crude product was purified further by stirring in 2 liters of a warm mixture of 1:1 acetone and isopropanol to afford a bright orange-yellow powder. This purified material had a melting point of 128 to 134° C., UV/vis wavelength maximum of 430 nm (toluene), and spectral strength in toluene of $5.37 \times 10^4$ milliliters per gram-centimeter. $^1$H-NMR spectral assignments (300 MHz, $CDCl_3$): 8.18 ppm (doublet, 2H integration, aromatic H), 8.05 ppm (doublet, 2H integration, aromatic H), 7.65 ppm (triplet, 2H integration, aromatic H), 7.30 ppm (triplet, 2H integration, aromatic H), 4.45 ppm (doublet of doublets, 4H integration, $CH_2$ adjacent ester), 4.00 ppm (doublet of doublets, 4H integration, $CH_2$ adjacent pyridone), 2.65 ppm (singlet, 6H integration, $CH_3$ on pyridone ring), 1.90–0.80 ppm (multiplets, CH, $CH_2$, $CH_3$ integrating for >60H, all other alkyl protons).

EXAMPLE V

A colorant of the formula shown in Example IVI was prepared as follows. A dimer ester anthranilate of the formula shown in Example IV was prepared as described in Example IV. Into a 1 liter three neck round bottom flask equipped with TEFLON®-coated mechanical stirrer, 125 milliliter pressure-equalized dropping funnel, and cold-temperature thermometer, was charged under agitation the dianthranilate (54.4 grams, 0.070 mol) followed with a prepared solution containing 173 milliliters of glacial acetic acid, 43 milliliters of deionized water, and 15 milliliters of concentrated sulfuric acid. The resulting brown solution was chilled to an internal temperature of +3 to +5° C. Nitrosyl-sulfuric acid (NSA, commercial solution containing 40 percent by weight NSA in sulfuric acid, obtained from Sigma-Aldrich Co., Milwaukee, Wis., 45.6 grams, 0.144 mol) was charged into the dropping funnel and then dripped slowly into the brown solution at a rate whereby the internal temperature was maintained between 0° C. and +8° C. After 20 minutes, the NSA addition was completed and the mixture was stirred for an additional 15 minutes while being cooled at 0° C. A portion of urea (0.2 grams, 3.3 mol) was then added to the mixture to quench any residual NSA reagent and the mixture was stirred for 15 minutes more until all the urea had dissolved.

A coupling solution of dodecyl pyridone was prepared in a 2 liter kettle equipped with mechanical TEFLON®-coated stirrer. Into this vessel was charged dodecyl pyridone (45.7 grams, 0.144 mol) prepared as described in Example IV, followed with 457 milliliters of isopropanol. A solution of sodium hydroxide (21.5 grams, 0.538 mol), sodium acetate trihydrate (73.2 grams, 0.538 mol), and 457 milliliters of deionized water was prepared and then added to the briskly stirred dispersion of the pyridone in isopropanol. A tea-brown transparent solution was formed after 15 minutes of stirring at room temperature. The cold diazonium salt solution was then slowly poured into the vigorously stirring dodecyl pyridone coupling solution. A bright yellow precipitate was formed instantly, and after complete addition of the diazonium salt solution, the yellow slurry was stirred an additional 30 minutes.

The yellow slurry was vacuum filtered through a 3 micron hydrophobic membrane media. The yellow dye cake was then redispersed into a 50:50 mixture of isopropanol and deionized water and stirred for 30 minutes. The filter cake was then subjected to the following treatment several times—redispersion into 1 liter of a 50:50 mixture of isopropanol and deionized water, stirring for 30 minutes, and filtration through 3 micron hydrophobic membrane—until the pH of the resulting filtrate was greater than 5.0 and the conductivity of the filtrate was below 10 microSiemens per centimeter. The filter cake was given two final rinses with 1 liter volumes of methanol. The cake was then dried in a vacuum-oven at 30° C. for 36 hours, affording 90 grams (89.6 percent yield) of the crude product as a mustard-yellow granular powder, melting point range of 121 to 133° C., UV/vis wavelength maximum of 430 nm (toluene) and spectral strength in toluene of $5.14 \times 10^4$ milliliters per gram-centimeter. If desired, this material can be further purified by recrystallization as described in Example V.

EXAMPLE VI

A colorant of the formula

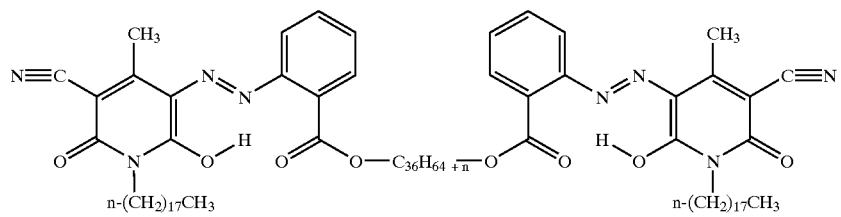

wherein $C_{36}H_{64+n}$ was a branched alkylene group which may include unsaturations and cyclic groups, wherein n is an integer of 0, 1, 2, 3, 4, 5, 6, 7, 8, 9, or 10, and wherein one isomer thereof was of the formula

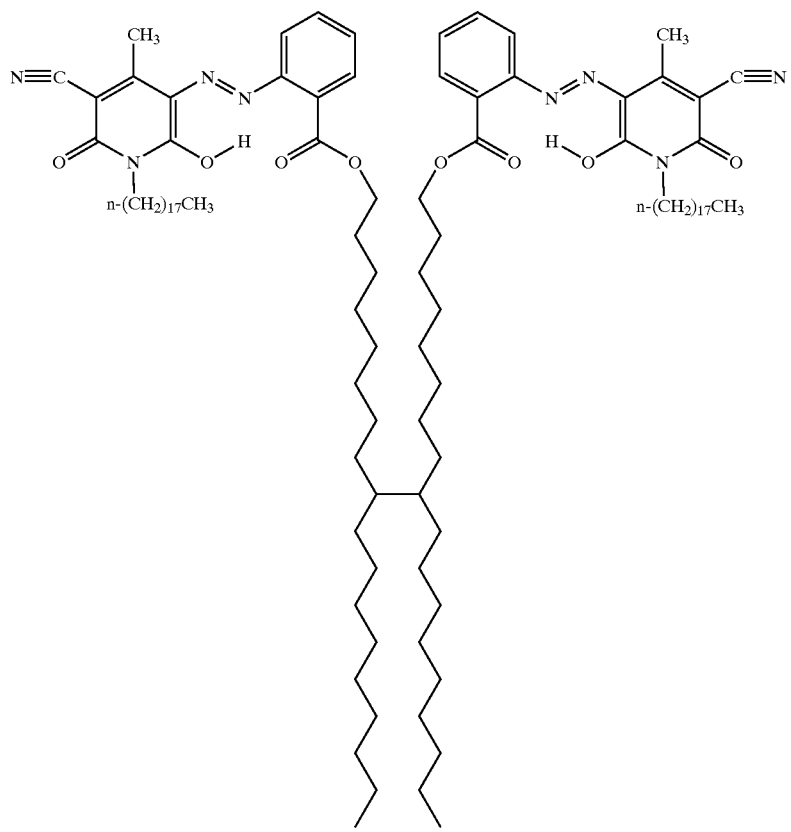
was prepared as follows.
A dimer ester anthranilate of the formula
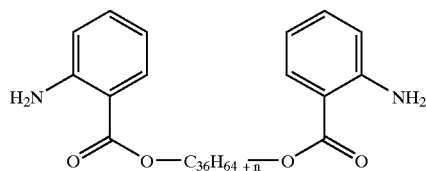
wherein $C_{36}H_{64+n}$ was a branched alkylene group which may include unsaturations and cyclic groups, wherein n is an integer of 0, 1, 2, 3, 4, 5, 6, 7, 8, 9, or 10, and wherein one isomer thereof was of the formula
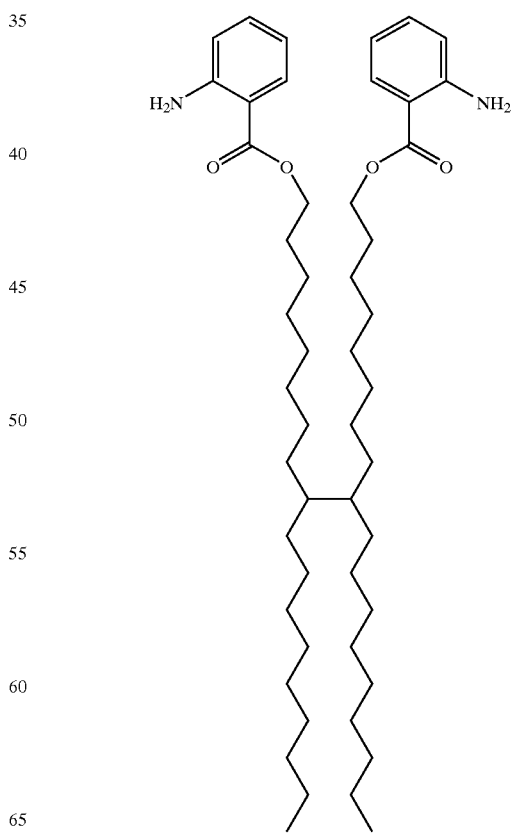
was prepared as described in Example IV.

Into a 2 liter Erlenmeyer flask equipped with magnetic stir bar and temperature thermostat was charged octadecylamine (stearylamine, 18.9 grams, 0.07 mol; obtained from Sigma-Aldrich Co., Milwaukee, Wis.) followed with ethyl cyanoacetate (7.9 grams, 0.07 mol, density 1.06 grams per milliliter; obtained from Spectrum Chemicals, New Brunswick, N.J.). The resulting colorless mixture was stirred and heated to 120° C. internal temperature for 1 hour, during which time a byproduct was distilled away. To the hot reaction mixture was then sequentially added ethyl acetoacetate (10.08 grams, 0.0775 mol, density 1.02 grams per milliliter, obtained from Lonza Group, Germany), piperidine (11.0 grams, 0.13 mol, density 0.861 grams per milliliter; obtained from Sigma-Aldrich Co.), and a solvent mixture (60 milliliters) containing 5 parts by weight toluene and 1 part by weight 1,2-dimethoxyethane. The reaction proceeded with stirring at 120° C. for another 24 hours. The solvents were then distilled off in vacuo, and the remaining viscous brown solution was carefully poured into a stirring solution of methanol (80 milliliters), deionized water (20 milliliters), and concentrated hydrochloric acid (16 milliliters, 2.5 mol). A solid tan precipitate formed instantly and the slurry was vacuum filtered followed by rinsing the solid cake with 2×50 milliliter portions of 80 percent aqueous methanol. The cake thus obtained was air-dried for 24 hours to afford 24.5 grams (0.061 mol, 87 percent yield) of N-stearyl pyridone product as light tan powder.

Into a 1 liter three neck round bottom flask equipped with a TEFLON® coated mechanical stirrer, 125 milliliter pressure-equalized dropping funnel, and cold-temperature thermometer was charged the dimer ester anthranilate prepared above (87 grams, 0.112 mol), followed sequentially with 170 milliliters of glacial acetic acid, 17 milliliters of concentrated sulfuric acid, 17 milliliters of deionized water, and 17 milliliters of propionic acid (obtained from Sigma-Aldrich Co.). The dark brown solution was chilled to an internal temperature of +3° C. to +5° C. while stirring. Nitrosylsulfuric acid (NSA, commercial solution containing 40 percent by weight NSA in sulfuric acid, obtained from Sigma-Aldrich Co.; 71 grams, 0.224 mol) was then charged into the dropping funnel and was dripped slowly into the anthranilate mixture so as to keep the internal temperature between +3° and +8° C. After 1 hour, the NSA addition was completed, and the mixture was stirred for an additional 0.5 hour while chilled. A small portion of sulfamic acid (1 gram, 0.01 mol) was then added to the mixture to quench any residual NSA, and the mixture was stirred for an additional 15 minutes.

The coupler solution of stearyl pyridone was prepared in a 4 liter flask equipped with mechanical stirrer. Into this vessel was charged sodium hydroxide (45 grams, 1.12 mol) and sodium acetate (92 grams, 1.12 mol), followed with deionized water (2 liters) and isopropanol (1.5 liter).Once all of the ingredients had dissolved, excess stearyl pyridone (139.5 grams, 0.35 mol) was added to the solution under vigorous agitation. The mixture was agitated for 30 minutes, after which any undissolved solids were removed by filtration through a micro-fiberglass membrane. The homogeneous pyridone solution was then transferred to a 10 liter glass vessel equipped with mechanical stirrer that was fitted with a TEFLON® coated stirring shaft. The cold diazonium salt solution was then slowly poured into the briskly stirring stearyl pyridone solution at room temperature. A bright yellow precipitate was formed instantly, and the slurry viscosity increased as more diazonium salt solution was added, requiring an additional 1.0 liter of deionized water to aid stirring. The acidic slurry (pH 2 to 3) was stirred for 1 hour prior to recovering the colorant material. The slurry was vacuum filtered through a 3 micron hydrophobic membrane media. All of the colorant material from the filter cake was then dissolved into 4 liters of dichloromethane solvent and divided into two 2 liter separatory funnels. Several extractions of the dichloromethane layer were performed using 1 liter portions of deionized water such that the final aqueous layer measured a pH of about 5 and a conductivity below 20 microSiemens per centimeter. The dichloromethane solvent was removed in vacuo by distillation, leaving a crude solid residue. The crude product was recrystallized in boiling isopropanol (about 3 liters) to afford a bright orange-yellow granular powder, melting point range of 122 to 123° C. $^1$H-NMR spectral analysis showed this material to be of high purity in accordance with the structure shown.

Other embodiments and modifications of the present invention may occur to those of ordinary skill in the art subsequent to a review of the information presented herein; these embodiments and modifications, as well as equivalents thereof, are also included within the scope of this invention.

The recited order of processing elements or sequences, or the use of numbers, letters, or other designations therefor, is not intended to limit a claimed process to any order except as specified in the claim itself.

What is claimed is:

1. A process for preparing dianthranilate compounds which comprises (a) admixing reactants as follows: (1) a diol of the formula $R_1(OH)_2$, wherein $R_1$ is an alkylene group having at least about 20 carbon atoms, and wherein the —OH groups are primary or secondary, (2) isatoic anhydride, present in an amount of at least about 2 moles of isatoic anhydride per every one mole of diol, (3) a catalyst which is 1,4-diazabicyclo[2.2.2]octane, N,N,N', N'-tetramethylethylene diamine, or a mixture thereof, said catalyst being present in an amount of at least about 0.2 mole of catalyst per every one mole of diol, and (4) a solvent; and (b) heating the mixture thus formed to form a dianthranilate compound of the formula

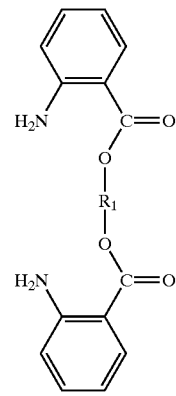

2. A process according to claim 1 wherein $R_1$ has at least about 30 carbon atoms.

3. A process according to claim 1 wherein $R_1$ has 36 carbon atoms.

4. A process according to claim 1 wherein $R_1$ is a branched alkyl group of the formula —$C_{36}H_{64+n}$— wherein n is an integer of 0, 1, 2, 3, 4, 5, 60, 7, 8, 9, or 10, which may include unsaturations and cyclic groups.

5. A process according to claim 1 wherein $R_1$ is of the formula

[structure: branched alkyl diyl group with two CH$_3$ termini]

6. A process according to claim 1 wherein the diol is of the formula

[structure: long-chain diol with HO and OH termini]

7. A process according to claim 1 wherein the isatoic anhydride and the diol are present in relative amounts of at least about 2.2 moles of isatoic anhydride per every one mole of diol.

8. A process according to claim 1 wherein the isatoic anhydride and the diol are present in relative amounts of no more than about 2.5 moles of isatoic anhydride per every one mole of diol.

9. A process according to claim 1 wherein the catalyst is 1,4-diazabicyclo[2.2.2]octane.

10. A process according to claim 1 wherein the catalyst is present in an amount of at least about 0.25 mole of catalyst per every one mole of diol.

11. A process according to claim 1 wherein the catalyst is present in an amount of at least about 0.5 mole of catalyst per every one mole of diol.

12. A process according to claim 1 wherein the catalyst is present in an amount of no more than about 0.5 mole of catalyst per every one mole of diol.

13. A process according to claim 1 wherein the reactants are insoluble in the solvent, resulting in a heterogeneous reaction mixture.

14. A process according to claim 1 wherein the solvent is toluene.

15. A process according to claim 1 wherein the diol and the solvent are present in relative amounts of at least about 0.5 mole of diol per liter of solvent.

16. A process according to claim 1 wherein the diol and the solvent are present in relative amounts of at least about 0.75 mole of diol per liter of solvent.

17. A process according to claim 1 wherein the diol and the solvent are present in relative amounts of no more than about 0.75 mole of diol per liter of solvent.

18. A process according to claim 1 wherein the mixture is heated to a temperature of at least about 40° C.

19. A process according to claim 1 wherein the mixture is heated to a temperature of no more than about 200° C.

20. A process according to claim 1 wherein the mixture is heated for a period of at least about 2.5 hours.

21. A process according to claim 1 wherein the mixture is heated for a period of no more than about 3.5 hours.

22. A process according to claim 1 wherein subsequent to formation of the dianthranilate compound excess isatoic anhydride is quenched by the addition of aqueous sodium hydroxide, aqueous potassium hydroxide, methanol, ethanol, or mixtures thereof.

23. A process according to claim 1 wherein the dianthranilate compound is separated from the mixture by liquid-liquid extraction.

24. A process according to claim 1 wherein the dianthronilate compound is separated from the mixture by addition of a non-solvent, thereby causing precipitation of the dianthranilate compound.

25. A process for preparing dianthranilate compounds which comprises (a) admixing reactants as follows: (1) a diol of the formula $R_1(OH)_2$, wherein $R_1$ is an alkylene group having about 36 carbon atoms, and wherein the —OH groups are primary or secondary, (2) isatoic anhydride, present in an amount of at least about 2.2 moles of isatoic anhydride per every one mole of diol and present in an amount of no more than about 2.5 moles of isatoic anhydride per every one mole of diol, (3) a catalyst which is 1,4-diazabicyclo[2.2.2]octane, said catalyst being present in an amount of at least about 0.25mole of catalyst per every one mole of diol, and (4) a toluene solvent, wherein the reactants are insoluble in the solvent, resulting in a heterogeneous reaction mixture, wherein the diol and the solvent are present in relative amounts of at least about 0.5 mole of diol per liter of solvent; (b) heating the mixture thus formed to a temperature of at least about 40° C. and to a temperature of no more than about 200° C. for a period of at least about 2.5 hours and for a period of no more than about 3.5 hours to form a dianthranilate compound of the formula

[structure: dianthranilate ester with two H$_2$N-substituted benzoate groups linked through $R_1$]

(c) subsequent to formation of the dianthranilate compound, quenching excess isatoic anhydride by the addition of aqueous sodium hydroxide, aqueous potassium hydroxide, methanol, ethanol, or mixtures thereof; and (d) separating the dianthranilate compound from the mixture by liquid-liquid extraction.

26. A process for preparing a diazopyridone colorant which comprises (I) preparing a dianthranilate compound by (a) admixing (1) a diol of the formula $R_1(OH)_2$, wherein $R_1$ is an alkylene group having at least about 20 carbon atoms, and wherein the —OH groups are primary or secondary, (2) isatoic anhydride, present in an amount of at least about 2 moles of isatoic anhydride per every one mole of diol, (3) a catalyst which is 1,4-diazabicyclo[2.2.2]octane, N,N,N',N'-tetramethylethylene diamine, or a mixture thereof, said catalyst being present in an amount of at least about 0.2 mole of catalyst per every one mole of diol, and (4) a solvent; and (b) heating the mixture thus formed to form a dianthranilate compound of the formula

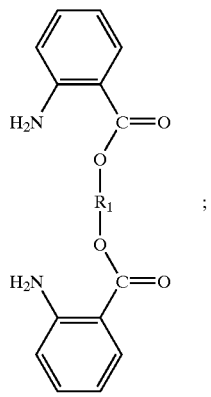

(II) reacting the dianthranilate compound with nitrosylsulfuric acid to form a diazonium salt of the formula

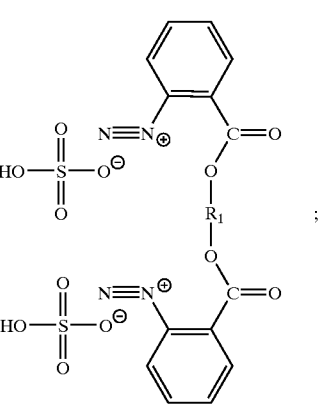

and (III) reacting the diazonium salt with a pyridone compound of the formula

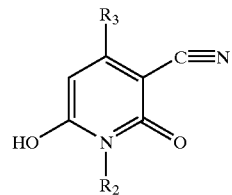

wherein $R_2$ is (i) an alkyl group, (ii) an aryl group, (iii) an arylalkyl group, (iv) an alkylaryl group, (v) an alkoxy group, (vi) an aryloxy group, (vii) an arylalkyloxy group, (viii) an alkylaryloxy group, (ix) a polyalkyleneoxy group, (x) a polyaryleneoxy group, (xi) a polyarylalkyleneoxy group, (xii) a polyalkylaryleneoxy group, (xiii) a heterocyclic group, (xiv) a silyl group, (xv) a siloxane group, (xvi) a polysilylene group, (xvii) a polysiloxane group, or (xviii) a group of the formula

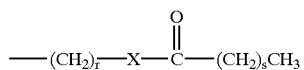

wherein r and s are each, independently of the other, integers representing a number of repeat —$CH_2$— groups, and $R_3$ is (i) an alkyl group, (ii) an aryl group, (iii) an arylalkyl group, or (iv) an alkylaryl group, to form a diazopyridone compound of the formula

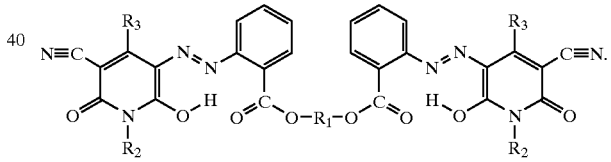

* * * * *